US007109178B2

(12) United States Patent
Ji et al.

(10) Patent No.: US 7,109,178 B2
(45) Date of Patent: Sep. 19, 2006

(54) METHOD FOR LIGATING NUCLEIC ACIDS AND MOLECULAR CLONING

(75) Inventors: Henry Ji, San Diego, CA (US); Alan Greener, San Diego, CA (US); Joseph A. Sorge, Wilson, WY (US); John Bauer, San Diego, CA (US); Richard Gibbs, Houston, TX (US); Carsten-Peter Carstens, La Jolla, CA (US)

(73) Assignee: Stratagene California, La Jolla, CA (US)

( * ) Notice: Subject to any disclaimer, the term of this patent is extended or adjusted under 35 U.S.C. 154(b) by 331 days.

(21) Appl. No.: 10/057,050

(22) Filed: Jan. 25, 2002

(65) Prior Publication Data
US 2002/0182731 A1   Dec. 5, 2002

Related U.S. Application Data

(63) Continuation of application No. 09/513,710, filed on Feb. 25, 2000, now abandoned.

(51) Int. Cl.
A61K 31/711 (2006.01)
(52) U.S. Cl. .................. 514/44; 435/462; 435/455; 435/91.41
(58) Field of Classification Search .................. 435/6, 435/462, 463
See application file for complete search history.

(56) References Cited

U.S. PATENT DOCUMENTS

| | | | |
|---|---|---|---|
| 4,959,317 A | 9/1990 | Sauer | |
| 5,731,182 A | 3/1998 | Boyce | |
| 5,763,240 A | 6/1998 | Zarling et al. | |
| 5,766,891 A * | 6/1998 | Shuman | 435/91.41 |
| 5,888,732 A | 3/1999 | Hartley et al. | |
| 6,087,170 A | 7/2000 | Kemble | |
| 6,825,011 B1 | 11/2004 | Romantchikov | 435/91.41 |

FOREIGN PATENT DOCUMENTS

| | | |
|---|---|---|
| WO | WO 98/56943 | 12/1998 |
| WO | WO 00/05355 | 2/2000 |
| WO | WO 00/36088 | 6/2000 |

OTHER PUBLICATIONS

Heyman et al Genome Research Genome-scale cloning and expression of individual opn reading frames using topoisomerase mediatedligation 9:383-392 1999.*
Pan et al Ligation of on synthetic activated DNA substrates by site-specific recombinases and topoisomerase I J. Biol Chem. 225:890-901 1993.*
Sambrook et al. (Molecular Cloning pp. 13-15 1982.*
Cheng, C. et al., (2000), "DNA strand transfer catalyzed by vaccinia topoisomerase: ligation of DNAs containing a 3' mononucleotide overhang", *Nucleic Acids Research* 28(9):1893-1898.
European Search Report of European Application No. 01918206.2.
Heyman, J.A. et al., (1999), "Genome-Scale cloning and expression of individual opem reading frames using topoisomerase I-mediated ligation", *Genome Research.*, 9:383-392.
Mondragon, A. et al., (1999) "The structure of *Escherichia coli*DNA topoisomerase III", *Structure*, 7:1373-1383.
Rybchin, V. et al., (1999), "The plasmid prophase N15: a linear DNA with covalently closed ends.", *Molecular Microbiology*, 33:895-903.
Meinhardt, F. et al., (1997). "Microbial linear plasmids." *Appl. Microbiol. Biotechnol.*, 47:329-336.
Hanai, R. et al., (1996), "Human TOP3: A single-copy gene encoding DNA topoisomerase III", *National Academy of Sciences*, 93:3653-3657.
Fukuhara, H., (1995), "Linear DNA plasmids of yeasts", *ELSEVIER.*, 131:1-9.
Higgins, R. et al., (1995), "Interaction of Terminase, the DNA Packaging Enzyme of Phage λ, with its *cos* DNA Substrate", *Journal of Molecular Biology*, 252:31-46.
Aslanidis, C. et al., (1994), "Minimal Length Requirements of the Single-stranded Tails for Ligation-independent Cloning (LIC) of PCR Products", *Cold Spring Harbor Laboratory Press ISSN*, 4:172-177.
Higgins, R. et al., (1994). "Chromosome end formation in phage λ, catalyzed by terminase, is controlled by two DNA elements of *cos, cos*N and R3 and by ATP", *Embo Journal*, 13:6152-6161.
Mukherjee, S. et al., (1994), "Purification and Characterization of a Eukaryotic Type 1 Topoisomerase from Pea Chloroplast", *Journal of Biological Chemistry*, 269:3739-01.
Nadal, M. et al., (1994), "Purification and Characterization of Reverse Gyrase from Sulfolobus shibatae", *Journal of Biological Chemistry*, 269:5255-5263.
Baubonis, W. et al., (1993), "Genomic targeting with purified Cre recombinase", *Nucleic Acids Research*, 21:2025-2029.
Cue, D. et al., (1993), "The Role of *cos*B, the Binding Site for Terminase, the DNA Packaging Enzyme of Bacteriophase λ, in the Nicking Reaction", *Journal of Molecular Biology*, 234:594-609.
Cue, D. et al., (1993), "A site required for termination of packaging of the phage λ chromosome", N*ational Academy of Sciences*, 90:9290-9294.
Hinnebusch, J. et al., (1993), "Linear plasmids and chromosomes in bacteria" *Molecular Microbiology*, 10:917-922.
Pan, et al., (1993), "Ligation of synthetic activated DNA substrates by site-specific recombinatses and topoisomerase I", *J. Biol. Chem.*, 268(5):3683-3689.

(Continued)

*Primary Examiner*—James Ketter
(74) *Attorney, Agent, or Firm*—Kathleen M. Williams; Mark J. FitzGerald; Edwards Angell Palmer & Dodge, LLP

(57) ABSTRACT

The invention provides methods of covalently joining nucleic acid molecules and methods of molecular cloning. The methods provide either sequential or simultaneous ligation of flanking or vector nucleic acid molecules to nucleic acid insert molecules by topoisomerase and DNA ligase. The methods provide for directional and non-directional covalent joining and cloning of nucleic acid molecules.

6 Claims, 15 Drawing Sheets

OTHER PUBLICATIONS

Sauer, B., (1993), "Manipulation of Transgenes by Site-Specific Recombination: Use of Cre Recombinase", *Academic Press, Inc.*, 225:890-901.

Fukushige, S. et al., (1992), "Genomic targeting with a positive-selection *lox* integration vector allows highly reproducible gene expression in mammalian cells", *National Academy of Sciences*, 89:7905-7909.

Kim, R. et al., (1992), "Identification of the Yeast TOP3 Gene Product as a Single Strand-specific DNA Topoisomerase", *Journal of Biology Chemistry*, 267:17178-17185.

Bouthier, C. et al., (1991), "Reverse Gyrase in Thermophilic Eubacteria", *Journal of Bacteriology*, 173:3921-3923.

Fukata, H. et al., (1991), "Chloroplast DNA Topoisomerase I from Cauliflower", *Journal of Biochemistry*, 109:127-131.

Slesarevi, A.I. et al., (1991), "DNA Topoisomerase III from Extremely Thermophilic Archaebacteria", *Journal of Biological Chemistry*, 19:12321-12328.

Aslanidis, C. et al., (1990), "Ligation-independent cloning of PCT products (LIC-PCR)", *Nucleic Acids Research*, 18:6069-6074.

Shuman, S. et al., (1987), "Identification of a vaccinia virus gene encoding a type I DNA topoisomerase", *National Academy of Sciences*, 84:7478-7482.

International Search Report of International Application No. PCT/US00/05657.

* cited by examiner

US 7,109,178 B2

SEQUENCE LISTING

<160> NUMBER OF SEQ ID NOS: 2

<210> SEQ ID NO 1
<211> LENGTH: 6
<212> TYPE: DNA
<213> ORGANISM: Vaccinia virus

<400> SEQUENCE: 1 ctcctt                                                          6

<210> SEQ ID NO 2
<211> LENGTH: 34
<212> TYPE: DNA
<213> ORGANISM: Artificial sequence
<220> FEATURE:
<223> OTHER INFORMATION: loxP site consensus sequence

<400> SEQUENCE: 2
ataacttcgt ataatgtatg ctatacgaag ttat                           34

METHOD FOR LIGATING NUCLEIC ACIDS AND MOLECULAR CLONING

This application is a continuation of U.S. patent application Ser. No. 09/513,710, filed Feb. 25, 2000, now abandoned which application is incorporated herein by reference in its entirety, including any and all tables and figures.

TECHNICAL FIELD

The invention relates to methods of covalently joining nucleic acid molecules and methods of molecular cloning of nucleic acid molecules.

BACKGROUND OF THE INVENTION

Construction of recombinant nucleic acid molecules requires two enzymatic steps. First, site-specific restriction endonuclease digestion or PCR amplification are used to generate linear nucleic acid molecules with defined termini. Second, the linear molecules are covalently joined at their termini in the presence of a ligase enzyme. Methods of covalently joining and cloning nucleic acid molecules that require only one step or that eliminate the use of restriction endonucleases or ligases would be advantageous over the traditional method of constructing recombinant nucleic acid molecules.

SUMMARY OF THE INVENTION

It is an object of the invention to provide methods of covalently joining nucleic acid molecules. It is a further object of the invention to provide methods of cloning nucleic acid molecules. This and other objects of the invention are provided by one or more of the embodiments described below.

One embodiment of the invention provides a method of covalently joining a nucleic acid insert molecule to first and second nucleic acid flanking molecules to form a ligated molecule. The method comprises incubating the insert molecule and the flanking molecules under conditions which permit their covalent joining to form a ligated molecule wherein an insert molecule is positioned between the first and the second flanking molecule. Each end of the insert molecule comprises a 5'-hydroxyl group. One end only of each of the first and second flanking molecules comprises a covalently bound topoisomerase polypeptide.

Another embodiment of the invention provides a method of covalently joining a nucleic acid insert molecule to first and second nucleic acid flanking molecules to form a ligated molecule. The method comprises incubating an insert molecule, wherein one end of the insert molecule comprises a 5'-hydroxyl group and the other end comprises a 5'-phosphate group, with the first flanking molecule, wherein one end only of the first flanking molecule comprises a covalently bound topoisomerase polypeptide. The incubation is done under conditions which permit their covalent joining to form a ligated nucleic acid wherein the insert molecule is positioned adjacent to the first flanking molecule. This ligated nucleic acid is incubated with phosphatase under conditions which permit removal of a 5'-phosphate group from the ligated nucleic acid. The ligated nucleic acid is incubated with the second flanking molecule. One end only of the second flanking molecule comprises a covalently bound topoisomerase polypeptide. The incubation is done under conditions which permit covalent joining to form a ligated molecule where the insert molecule is positioned between the first and the second flanking molecule.

In still another embodiment of the invention a method of covalently joining a nucleic acid insert molecule to first and second nucleic acid flanking molecules to form a ligated molecule is provided. The method comprises incubating an insert molecule and flanking molecules under conditions which permit their covalent joining to form a ligated molecule wherein an insert molecule is positioned between the first and the second flanking molecule. One end of the insert molecule comprises a 5'-hydroxyl group and the other end comprises a 5'-phosphate group. One end only of the first flanking molecule comprises a covalently bound topoisomerase polypeptide and one end of the second flanking molecule comprises a ligase substrate site.

Any of the first and second nucleic acid flanking molecules can together comprise a pair of left and right vector arms. Further, the ends of the vector arms not covalently joined to the insert can be covalently or non-covalently joined to each other by a method selected from the group consisting of nucleic acid ligase mediated ligation, complementary sequence annealing, topoisomerase mediated ligation, in vitro site-specific recombination, in vivo site-specific recombination, and in vivo homologous recombination.

In still another embodiment of the invention a method of molecular cloning is provided. The method comprises incubating a nucleic acid insert molecule comprising a 5'-hydroxyl group at one end and a 5'-phosphate at the other end, and a linear cloning vector. The linear cloning vector comprises a covalently bound topoisomerase polypeptide at one end only and a ligation substrate site at the other end. The incubation is done under conditions sufficient for their covalent joining to form a ligated circular vector. The ligated circular vector is transformed into a host cell.

Another embodiment of the invention provides a method for molecular cloning. The method comprises incubating a nucleic acid insert molecule where each end of the insert molecule comprises a 5'-hydroxyl group with a first and a second linear arm where one end only of each of the first and second linear arms comprises a covalently bound topoisomerase and the other end comprises a cloning substrate site. The incubation is done under conditions sufficient for their covalent joining to form a ligated insert molecule where the insert molecule is positioned between the first and the second linear arm. The ligated insert molecule is transformed into a host cell.

Even another embodiment of the invention provides a method for molecular cloning. A nucleic acid insert molecule, wherein one end of the insert molecule comprises a 5'-hydroxyl group and the other end comprises a 5'-phosphate group, and a first linear arm, wherein one end only of the first linear arm comprises a covalently bound topoisomerase polypeptide and the other end comprises a cloning substrate site are incubated together. The incubation is done under conditions which permit their covalent joining to form a ligated nucleic acid wherein the insert molecule is positioned adjacent to the first linear arm. The ligated nucleic acid is incubated with phosphatase under conditions which permit removal of a 5'-phosphate group from the ligated nucleic acid. The ligated nucleic acid is incubated with a second linear vector arm, wherein one end only of the second linear vector arm comprises a covalently bound topoisomerase polypeptide and the other end comprises a cloning substrate site. The incubation is done under conditions which permit covalent joining to form a ligated insert molecule wherein the insert molecule is positioned between the first and the second linear vector arm. The ligated insert molecule is transformed into a host cell.

In yet another embodiment of the invention a method for molecular cloning is provided comprising incubating a nucleic acid insert molecule, wherein one end of the insert molecule comprises a 5'-hydroxyl group and the other end comprises a 5'-phosphate group; a first linear arm, wherein one end only of the first linear arm comprises a covalently bound topoisomerase polypeptide and the other end comprises a cloning substrate site; and a second linear arm, wherein one end of the second linear arm comprises a ligase substrate site and the other end comprises a cloning substrate site. The incubation is done under conditions which permit their covalent joining to form a ligated insert molecule wherein the insert molecule is positioned between the first and the second linear arm. The ligated insert molecule is transformed into a host cell.

The cloning substrate site can be selected from the group consisting of a cos site, a LIC site, and a loxP site.

Where the cloning substrate site is loxP, the method can further comprise incubating in vitro the ligated insert molecule with a Cre recombinase and a circular plasmid comprising a loxP site. The incubation is done under conditions sufficient for site-specific recombination to form a circular plasmid comprising the ligated insert molecule. The circular plasmid comprising the ligated insert molecule is transformed into a host cell.

Where the cloning substrate site is loxP the method can further comprise transforming the ligated insert molecule into a host cell comprising a circular plasmid comprising a loxP site, wherein the cell expresses Cre recombinase. The transformation is done under conditions sufficient for site-specific recombination to form a circular plasmid comprising the ligated insert molecule within the cell.

Where the cloning substrate site is a site for homologous recombination with a circular plasmid vector the transformation step further comprises transforming the ligated insert molecule into a host cell comprising a circular plasmid vector. The circular plasmid vector comprises a site for homologous recombination with the ligated insert molecule, and the host cell is recA+. The transformation is done under conditions sufficient for homologous recombination to form a circular plasmid comprising the ligated insert molecule within the host cell.

The first linear arm can comprise a left lambda arm comprising at one end only a covalently bound topoisomerase. The second linear arm can comprise a right lambda arm comprising at one end only a covalently bound topoisomerase.

As used herein, the term "join" or "joining" refers to both covalent and noncovalent attachment of one nucleic acid to another, or one end of a nucleic acid to another end of a nucleic acid. "Covalent" joining refers to the attachment of one end of a nucleic acid strand to another end of a nucleic acid strand via a phosphate bond or to attachment of one end of a double-stranded nucleic acid to another double-stranded end via phosphate bonding on one or both strands. "Non-covalent" joining refers to attachment of one end of a nucleic acid to another end via annealing of a single-stranded regions to each other; that is, no phosphate bond is generated in this embodiment.

"Ligate" or "ligated" refers to the covalent joining of two ends of one or more nucleic acid molecules.

"Complementary annealing" refers to annealing, or the pairing of bases, of complementary regions of one or more nucleic acids, and thus to the formation of hydrogen bonds and other non-covalent interactions between pairs of bases.

A "topoisomerase" is a polypeptide that is capable of covalently joining to at least one strand of a nucleic acid molecule and ligating that strand to another strand, as described hereinbelow. Topoisomerase according to the invention comprises type I topoisomerases.

"Bound to" refers to a covalent bonding of a topoisomerase polypeptide to a nucleic acid molecule.

"Nucleic acid molecule" refers to a double-stranded nucleic acid, unless otherwise specified.

"One end only" refers to the presence of a topoisomerase polypeptide at one end of a nucleic acid molecule, where the nucleic acid molecule contains two ends.

The term "site" is meant to designate a contiguous stretch of nucleotides, e.g., 1–100 bases in length, usually 5–25 bases in length, e.g., 8–16 bases, that is susceptible to (i.e., a substrate for) modification by an enzyme that modifies nucleic acids, e.g., a ligase or a restriction enzyme.

A "cloning substrate site", as used herein, is a site occurring on a nucleic acid molecule for the covalent or non-covalent joining of nucleic acid sequences or for recombination. Examples of cloning substrate sites include cos sites, LIC sites, sites for site-specific recombination, such as lambda attachment elements or loxP sites, sites for homologous recombination, and ligation substrate sites.

A "ligation substrate site", as used herein, is a site occurring on a nucleic acid molecule of the invention that is capable of becoming covalently joined to another nucleic acid molecule in the presence of a ligase enzyme, such as DNA ligase.

A "vector arm" or a "linear arm", as used herein, is a linear nucleic acid molecule, and is preferably a portion or fragment of a bacteriophage or plasmid genome.

"Directional" cloning refers to a cloning method in which, by selecting steps in the method, one can obtain a desired orientation of a given nucleic acid molecule upon cloning into another nucleic acid molecule or between two other nucleic acid molecules; as used herein, "orientation" may refer to 5' to 3' with reference to a given open reading frame or a given control region or a known sequence. Thus, for example, an insert molecule may contain an open reading frame having a 5'-3' orientation with respect to transcription and the insert molecule may be directionally cloned between a left and right vector arms such that the ligated (cloned) molecule comprises, from 5' to 3': left vector arm, 5' insert 3', right vector arm. "Non-directional" cloning refers to cloning methods which produce a ligated molecule in which the insert, for example, appears between the two arms in either orientation.

DETAILED DESCRIPTION OF THE INVENTION

Insert Polynucleotide Molecules

Figure 1:
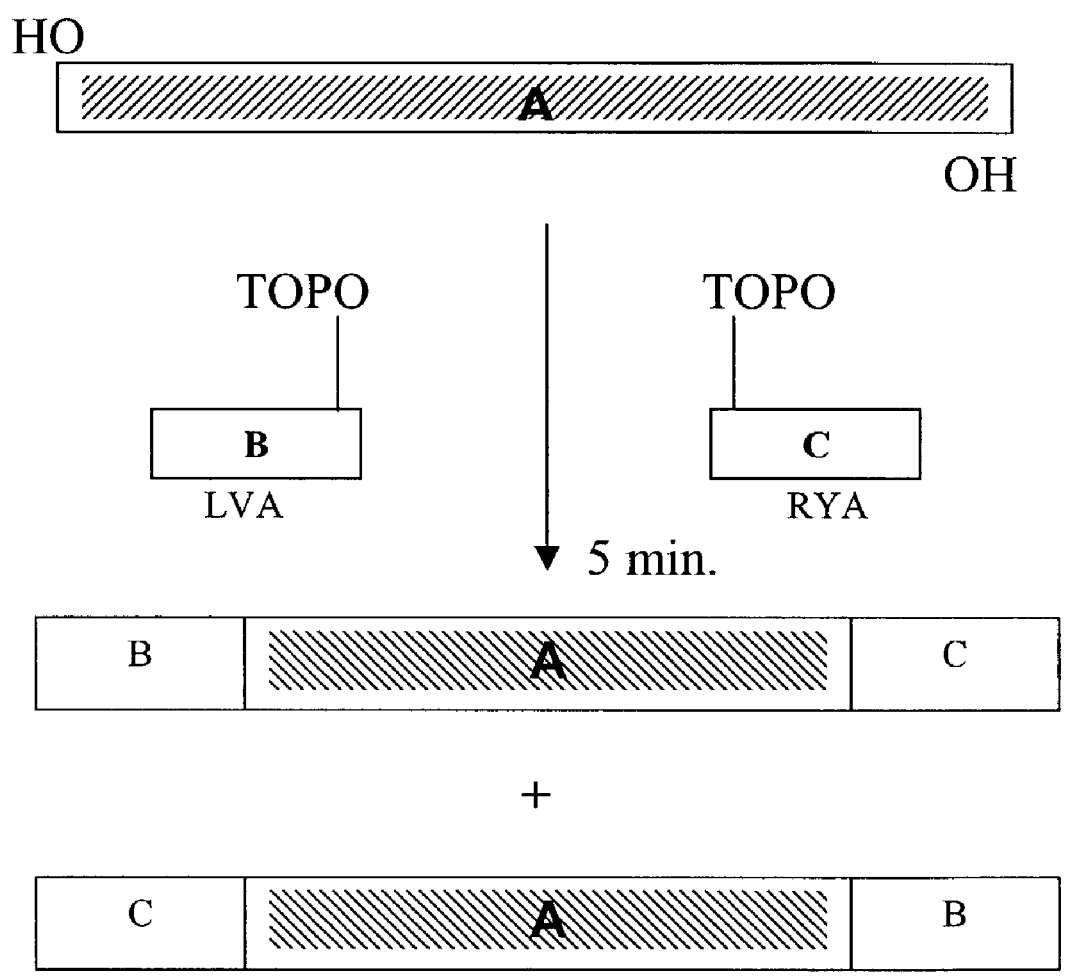
FIG. 1 shows the non-directional covalent joining of an insert molecule with 5'-OH groups on each end to a right vector arm and a left vector arm each comprising a topoisomerase polypeptide on one end only.

Insert polynucleotide molecules comprise isolated and purified double-stranded DNA, double-stranded RNA, or double-stranded DNA/RNA hybrid nucleic acids. An insert molecule can be a full-length molecule or a fragment of a full-length molecule. Further, an insert molecule can be naturally-occurring, i.e., found in nature or recombinant.

Preferably, insert polynucleotides are isolated free of other components, such as proteins and lipids. Insert polynucleotides can be made by a cell and isolated or can be synthesized in the laboratory, for example, using an automatic synthesizer or an amplification method such as PCR. Where an insert polynucleotide is prepared by PCR, the insert is generated using a pair of primers comprising a 3'-primer and a 5'-primer. Both the 3'-primer and the 5'-primer can comprise a 5'-hydroxyl group to produce an insert with 5'-hydroxyl groups (5'-OH) on both ends. Alternatively, one of the primers can comprise a 5'-hydroxyl group and one can comprise a 5'-phosphate group to produce an insert with a 5'-OH group on one end and a 5'-phosphate (5'-P) group on the other end. Optionally, both the 3'-primer and the 5'-primer can comprise a 5'-phosphate group to produce an insert with 5'-P groups on both ends.

Molecules Flanking an Insert Molecule

An insert polynucleotide molecule can be covalently joined to several types of molecules, such as a double-stranded DNA, a double-stranded RNA, and a double-stranded DNA/RNA hybrid molecule. Preferably, an insert polynucleotide molecule is covalently joined to a vector molecule or to vector molecules such as a linear arm of a plasmid or bacteriophage. Vectors suitable for ligation of an insert molecule include bacteriophage, such as bacteriophage lambda, including, but not limited to lambda insertion vectors such as Lambda ZAP®II vector, ZAP Express® vector, Lambda ZAP®-CMV vector (Stratagene), lambda gt10, and lambda gt11. Lambda replacement vectors, for example Lambda FIX®II vector, Lambda DASH®II vector, and Lambda EMBL3 and Lambda EMBL4 (Stratagene) can also be used as vectors.

Both prokaryotic and eukaryotic linear plasmids can be used as vectors. See e.g., Meinhardt et al. (1997) Appl. Microbiol. Biotechnol. 47:329–36; Fukuhara, (1995) FEMS Microbiol. Lett. 131:1–9; Hinnebusch & Tilly, (1993) Mol Microbiol. 10:917–22. For example, the plasmid prophage N15 of *E. coli* is a suitable linear plasmid vector. See Rybchin & Svarchevsky (1999) Mol. Microbiol. 33:895–903.

Vector nucleic acid polynucleotides, such as bacteriophage and plasmids can be isolated and purified from cells carrying these elements according to methods well known in the art. See e.g. MOLECULAR CLONING: A LABORATORY MANUAL (Sambrook et al., eds., Cold Spring Harbor Laboratory Press, Cold Spring Harbor, 1989) and Ausubel (CURRENT PROTOCOLS IN MOLECULAR BIOLOGY (Ausubel et al., eds., John Wiley & Sons, New York, 1987)). Additionally, many bacteriophage and plasmid vectors are commercially available. The bacteriophage or plasmid nucleic acid can be prepared, if necessary by cleavage with an appropriate restriction enzyme such that the digested bacteriophage or plasmid nucleic acid is compatible with an insert molecule.

Preferably, an insert molecule is covalently joined to right and left lambda linear vector arms such that the insert molecule is positioned between right and left lambda linear vector arms. In lambda insertion vectors, a left vector arm can comprise lambda nucleic acids occurring to the left of the insertion site and a right vector arm can comprises lambda nucleic acids occurring to the right of the insertion. In lambda replacement vectors, a left lambda arm comprises lambda nucleic acid occurring to the left of the nucleic acids to be replaced by the insert nucleic acids and a right lambda arm comprises lambda nucleic acids occurring to the right of the nucleic acids to replaced by the insert nucleic acids. Lambda vectors can vary in nucleic acid sequence; however, the left arm can typically comprise the head and tail genes A–J, while the right arm can typically comprise from $p_R$ through a cosR site of a lambda genome.

Preferably, the vector or flanking molecule to which the insert is to be covalently joined is a linear molecule comprising a topoisomerase covalently linked to only one end of the linear molecule. A double-stranded DNA, double-stranded RNA, or double-stranded DNA/RNA molecule with one topoisomerase molecule bound to one end of the DNA or RNA molecule is a univalent molecule. DNA topoisomerases catalyze a conversion in the linking number of a double-stranded DNA molecule. The linking number is the number of times one DNA strand crosses over the second DNA strand in space. Type 1 topoisomerases act by making a transient break in one strand of a nucleic acid. A type 1 topoisomerase first binds to a nucleic acid and nicks one strand of the nucleic acid. A stable complex is formed where the free 3'-phosphate end of the nicked strand is covalently bound to a tyrosine residue of the enzyme. The second strand is pulled through the gap in the first strand and the gap is then sealed by the enzyme. The gap can be sealed at the same bond originally nicked or the complex can combine with a heterologous nucleic acid, such as an insert molecule, that has a 5'-hydroxy end. Where the complex is combined with a heterologous nucleic acid, a recombinant molecule is formed.

Type 1 topoisomerases include, but are not limited to *E. coli* topoisomerase I (Keck et al., (1999) Nat. Strut. Biol. 6:900), *E. coli* topoisomerase III (Mondragon et al., (1999) Structure Fold. Des. 7:1373), *S. cerevisiae* topoisomerase III (Kim et al., (1992) J. Biol. Chem. 267:17178), human topoisomerase III (Hanai et al., (1996) Proc. Natl. Acad. Sci. 93:3653), the type I topoisomerase from chloroplasts (Mukheijee et al. (1994) 269:3793; Fukata et al. (1991) J. Biochem (Tokyo) 109:127), thermophilic reverse gyrases (Nadal et al., (1994) J. Biol. Chem. 269:5255; Slesarev et al., (1991) J. Biol. Chem. 266:12321; Bouthier de la Tour et al., (1991) J. Bact. 173:3921), thermophilic *D. amylolyticus* topoisomerase III (Slesarev et al., (1991) J. Biol. Chem. 266:12321), and vaccinia DNA topoisomerase I (Shuman et al., (1987) Proc. Natl. Acad. Sci. 84:7478). Site-specific type I DNA topoisomerases are particularly useful in the invention. Site-specific type I DNA topoisomerases include vaccinia topoisomerase and pox virus topoisomerases.

A topoisomerase enzyme can be covalently linked to a vector or flanking molecule by, for example, the method of Heyman et al. (Genome Res. (1999) 9:383). Briefly, *Vaccinia* DNA topoisomerase cleaves the phosphodiester backbone of one strand of a nucleic acid at a consensus pentopyrimidine element: 5'-C/TCCTT-3' (SEQ ID NO:1). This element can be added onto the end of a vector or flanking molecule. Vaccinia topoisomerase can then be incubated with the vector or flanking molecule such that the topoisomerase becomes covalently bound to the underlined T in the C/TCCT̲T sequence. Optionally, nuclease treatment, such as exonuclease III treatment can be used to remove single strand ends from the element such that a blunt-ended insert fragment with topoisomerase bound to the molecule is formed.

Optionally, the molecule to which the insert is to be covalently joined is a linear molecule comprising a ligation substrate site at a first end of the linear molecule. A ligation substrate site comprises a site for nucleic acid ligation that is mediated by a ligase enzyme. A ligation substrate site can comprise any double-stranded nucleic acid that has blunt ends or protruding termini that can be covalently joined to another nucleic acid molecule in the presence of a ligase enzyme. Preferably, the ligation substrate site comprises a 5'-phosphate group and is complementary to one end of an insert molecule. A ligation substrate site can be produced by, for example cleaving a double-stranded nucleic acid molecule with a restriction enzyme that produces blunt-ended termini, 5'-protruding ends, or 3'-protruding ends and purifying the nucleic acid molecule. A ligation between a linear molecule comprising a ligation substrate site and an insert molecule takes place in the presence of a ligase enzyme such as bacteriophage T4 DNA ligase or Pfu DNA ligase (Stratagene).

Preferably, the vector or flanking molecule to which the insert is to be covalently joined is a linear molecule comprising a topoisomerase covalently linked to only one end of the molecule or a ligation substrate site at one end of the linear molecule. The second end of the linear molecule preferably comprises a cloning substrate site such as, a cos site, a LIC site, a site-specific recombination site (such as a loxP site or lambda attachment element), a homologous recombination site or a ligation substrate site.

A bacteriophage lambda genome has cos sites at the ends of the genome. See, LAMBDA II (Roger W. Hendrix, ed., Cold Spring Harbor Laboratory Press) 1983; Higgins et al., (1995) J. Mol. Biol. 252:31; Higgins et al., (1994) EMBO J. 13:6152; Cue et al., (1993) J. Mol. Biol. 234:594; Cue et al., (1993) Proc. Natl. Acad. Sci. USA 90:9290. Cleavage occurs at a left cos site (as defined on a standard lambda map) to generate a free end that is inserted into a capsid. The insertion of nucleic acid continues until a right cos site is encountered. Cleavage occurs at the right cos site to generate the second end. Any nucleic acid molecule that is contained between two cos sites can be packaged.

A nucleic acid molecule comprising a cos site, a fragment of a cos site, a mutant of a cos site, or a variant of a cos site can be isolated from a preparation of bacteriophage lambda DNA or may synthesized in the laboratory. A nucleic molecule comprising a cos site can be ligated to the end of the molecule to which the insert is to be covalently joined. Alternatively, a cos site can be added to the end of a molecule to which the insert is to be covalently joined using standard molecular biology cloning techniques such as PCR. In the methods of the invention distal ends (i.e., the ends of vector arms not covalently joined to an insert molecule) of vector arms containing terminal cos sites can be readily annealed to one another in *E. coli* host cells by virtue of their explicit sequence. cos sites do not appreciably anneal in vitro at room temperature.

A ligation-independent cloning (LIC) site can be any size, but is preferably 12 to 13 nucleotides or longer. Sites longer than 12–13 nucleotides may work more efficiently, e.g., up to 24 bases, or up to 48 bases or longer. See Aslanidis and de Jong, (1990) Nucleic Acids Res. 18:6069. The 12–13 nucleotide terminus can comprise any nucleic acid sequence; however, preferably one or none of the nucleotides of a 3' strand of the 12–13 nucleotide terminus is an adenosine. A nucleic molecule comprising a LIC site can be ligated to the ends of the vector or flanking molecule to which the insert is to be covalently joined. Alternatively, a LIC site can be added to the end of a vector or flanking molecule to which the insert is to be covalently joined using standard molecular biology cloning techniques, such as by PCR.

Where the second end of a linear molecule comprises a LIC site, a ligated insert/vector molecule will be formed that comprises LIC ends at each end of the ligated insert/vector molecule. The insert can then be joined to a LIC ready vector. Aslanidis et al., (1994) PCR Methods Appl. 4:172; Aslanidis and de Jong (1990) Nucleic Acids Res. 18:6069. Briefly, the ligated insert/vector molecule is subjected to treatment with, for example, Pfu DNA polymerase in the presence of dATP. In the absence of dTTP, dGTP, and dCTP, the 3'- to 5'-exonuclease activity of Pfu DNA polymerase removes 12 to 13 nucleic acids from the 3'-ends of the ligated insert/vector molecule. This activity continues until the first adenine is encountered. This produces a ligated insert/vector molecule with 5'-extended single-stranded tails that are complementary to the single-stranded tails of a LIC ready vector. The ligated insert/vector molecule will anneal to the LIC ready vector without further enzymatic treatment.

The second end of the linear molecule can further comprise a site for homologous recombination or a site for site-specific recombination. Homologous recombination is a recombination event occurring between homologous sequences of nucleic acids. The enzymes responsible for homologous recombination can use any pair of homologous sequences as substrates, although some types of nucleic acid sequences can be favored over others. Sites for homologous recombination comprise nucleic acid sequences that are homologous to the nucleic acid sequences of a cloning vector, such as a circular plasmid. The sites can insert (or integrate) into a cloning vector by homologous recombination, thereby inserting or displacing a nucleic acid sequence, or deleting a nucleic acid sequence altogether.

To create a homologous recombinant plasmid cloning vector, a plasmid cloning vector is prepared which contains homologous recombination nucleic acid sites that are substantially homologous to those sites occurring on the ligated insert/vector of interest. Substantially homologous nucleic acid sequences are those nucleic acid sequences that share sufficient nucleic acid sequence homology to provide for sufficient homologous recombination between a ligated insert/vector sequence and a plasmid cloning vector. Sufficient nucleic acid sequence homology is the amount which provides for homologous recombination at a frequency which allows for detection of plasmid cloning vectors in which homologous recombination and integration of the ligated vector/insert has occurred. Substantially homologous nucleic acid sequences preferably share regions with about 60% to 100% nucleic acid sequence homology, and more preferably about 75% to 100% homology in the nucleic acid sequence. A site for homologous recombination can be present in the plasmid cloning vector in two or more copies. The homologous recombination sites in the plasmid cloning vector are of sufficient length for successful homologous recombination with a ligated insert/vector molecule. Typically, each homologous recombination site is at least 30, 75, 100, 150, 250, 500, or 1000 base pairs. The ligated insert/vector sequence comprises these substantially homologous recombination sites at both the 5'- and 3-' ends. The ligated insert/vector sequence is transformed into a host cell, such as an *E. coli* cell that contains the plasmid cloning vector. Preferably, the host cell is RecA+. Rec A is the product of the recA locus of *E. coli* and is a protein that is involved in recombination.

In addition to homologous recombination as described above, enzyme-assisted site-specific integration systems are known in the art and can be applied to integrate a ligated nucleic acid insert/vector molecule at a predetermined location in a cloning vector molecule. Site-specific recombination is a recombination event between specific pairs or sequences. The recombination event involves specific sequences of nucleic acids comprising a short stretch of homology necessary for the recombination event. The enzymes involved in the recombination event will act only on this particular pair of target sequences. Examples of such enzyme-assisted integration systems include the Cre recombinase/loxP target system (e.g., as described in Baubonis and Sauer (1993) Nucl. Acids Res. 21:2025; and Fukushige and Sauer, (1992) Proc. Natl. Acad. Sci. USA 89:7905). A loxP site (locus of crossing over) comprises two 13 base pair inverted repeats separated by an 8 base pair asymmetric spacer region:

ATAACTTCGTATA ATGTATGC TATACGAAGT-TAT (SEQ ID NO:2)

Inverted repeat Spacer Inverted repeat

A loxP site of the invention comprises variants and mutants of this sequence that function to produce site-specific recombination. Cre is a 38 kDa recombinase protein from bacteriophage P1 which mediates intramolecular and intermolecular site-specific recombination between loxP sites. Sauer, (1993) Methods Enzymol. 225:890. A loxP site is an asymmetrical nucleotide sequence and two lox sites on the same DNA molecule can have the same or opposite orientation with respect to one another. See U.S. Pat. No. 4,959,317. Where two loxP sites occur in the same orientation on a nucleic acid molecule, recombination between the loxP sites results in the deletion of the nucleic acid segment located between the two loxP sites and a connection between the resulting ends of the original nucleic acid molecule. The deleted nucleic acid molecule will form a circular molecule of nucleic acid. The original nucleic acid molecule and the circular nucleic acid molecule will each contain a single loxP site. Where two loxP sites occur in opposite orientations on the same nucleic acid molecule recombination will result in an inversion of the nucleotide sequence of the nucleic acid segment located between the two loxP sites. Further, where two loxP sites occur on each of two nucleic acid segments, reciprocal exchange of nucleic acid segments proximate to the loxP sites can occur.

Methods of Covalently Joining

Insert polynucleotide molecules comprising a 5'-OH group on each end or a 5'-OH on one end and a 5'-phosphate group on the other end can be covalently joined to flanking polynucleotide molecules such that non-directional or directional covalent joining is achieved. Where an insert polynucleotide molecule has a 5'-OH group on each end non-directional covalent joining of the insert to flanking polynucleotide molecules results. For example, where an insert polynucleotide (I) with a 5'-OH group at each end is covalently joined to flanking molecules, for example, a left vector arm (LVA) and a right vector arm (RVA) each with a topoisomerase polypeptide covalently joined at only one end, the result will be non-directional covalent joining of the molecules. A LVA, RVA, and insert molecule are incubated together under conditions sufficient to permit their topoisomerase-mediated covalent joining to form a covalently joined nucleic acid molecule where the insert molecule is positioned between the LVA and RVA. Four different covalently joined products (ligated insert/vector molecules) will result: LVA-I-LVA, RVA-I-RVA, LVA-I-RVA, and RVA-I-LVA. Only the LVA-I-RVA and RVA-I-LVA products are viable replication competent entities.

Where an insert polynucleotide has a 5'-OH group on one end and a 5'-phosphate group on the other end directional covalent joining of the insert to flanking polynucleotide molecules can result. For example, where an insert polynucleotide is covalently joined to a flanking molecules such as a LVA and a RVA, each comprising a topoisomerase covalently bound to only one end, directional covalent joining of the molecules can result. A first vector arm, for example, a LVA is covalently joined to an insert molecule at the 5'-OH end by incubating a LVA and an insert molecule together under conditions sufficient to permit topoisomerase-mediated covalent joining to form a ligated nucleic acid molecule where the insert molecule is positioned adjacent to a LVA to create LVA-I-phosphate. The 5'-phosphate end of the insert is unable to be ligated to the LVA or RVA because either the LVA or RVA has a 3'-phosphate, which is the site to which a topoisomerase polypeptide is joined to the LVA and RVA. The LVA-I-5'-phosphate is treated with phosphatase, under conditions which permit removal of a 5'-phosphate group from the ligated nucleic acid resulting in a LVA-I-5'-OH molecule. The LVA-I-5'-OH molecule is then covalently joined to the RVA to form LVA-I-RVA by incubating a LVA-I-5'-OH molecule with a RVA under conditions which permit topoisomerase covalent joining to form a ligated molecule where the insert molecule is positioned between a RVA and a LVA (a ligated insert/vector molecule).

Alternatively, an insert polynucleotide comprising a 5'-OH group on one end and a 5'-phosphate group on the other end can be covalently joined in a directional manner to a flanking nucleic acid molecule comprising a topoisomerase polynucleotide on only one end and to a second flanking molecule comprising a ligation substrate site on one end. For example, an insert molecule can be covalently joined to a flanking nucleic acid molecule, such as a LVA, comprising a topoisomerase polypeptide on only one end and to, for example, a RVA comprising a ligation substrate end on one end. The insert LVA, and RVA are covalently joined by topoisomerase-mediated joining and ligase-mediated joining under conditions sufficient to form a ligated nucleic acid where the insert molecule is positioned between a LVA and a RVA to form LVA-I-RVA (a ligated insert/vector molecule). This reaction can take place in one step.

After the ligated insert/vector molecule described above has been constructed, the two vector arms can be non-covalently or covalently joined to one another, at the ends distal to the covalently attached topoisomerase polypeptide or ligation substrate site (i.e., at their free ends), by a number of methods such that a circular molecule is formed. For example, the ends of the ligated insert/vector molecule can comprise ligase substrate sites or complementary nucleic acid sequences such that the ends can be joined by ligase enzyme mediated ligation or complementary sequence annealing. Further, where the ends of the ligated insert/vector molecule comprise 5'-OH groups the ends can be joined by topoisomerase mediated ligation using a polynucleotide comprising a topoisomerase polypeptide at both ends of the polynucleotides. See e.g. U.S. Pat. No. 5,766, 891. Further, where the ends of the ligated insert/vector molecule comprise in vitro or in vivo site-specific recombination sites or in vivo homologous recombination sites the ligated insert/vector molecule can be recombined into a circular plasmid containing the same recombination sites.

The methods of directional and non-directional covalently joining of nucleic acid molecules are useful in, for example, end-labeling, ligand tagging, and molecular cloning.

Methods of Molecular Cloning

Insert polynucleotide molecules comprising a 5'-OH group on each end or a 5'-OH on one end and a 5'-phosphate group on the other end can be cloned into vector molecules such that non-directional or directional cloning is achieved.

Non-directional cloning can be accomplished by cloning a polynucleotide insert molecule comprising 5'-OH groups at both ends of the molecule into a nucleic acid vector. For example, an insert polynucleotide (I) with a 5'OH group at each end can be cloned into a vector, such as a left vector arm (LVA) and a right vector arm (RVA) where each vector arm has a topoisomerase polypeptide covalently joined at only one end of the vector arm. The result will be non-directional covalent joining of the molecules. Preferably, the LVA and RVA molecules have a cloning substrate site, such as a cos site, a LIC site, a loxP site, a site for homologous recombination, a site for site-specific recombination, or a ligase substrate site at the other end of the molecule. A LVA, RVA, and insert molecule are incubated together under conditions sufficient for topoisomerase-mediated covalent joining of the molecules to form a ligated nucleic acid wherein the insert molecule is positioned between the LVA and RVA. Four different covalently joined products will result: LVA-I-LVA, RVA-I-RVA, LVA-I-RVA, and RVA-I-LVA (ligated insert/vector molecules). Only the LVA-I-RVA and RVA-I-LVA products are viable replication competent entities.

Directional cloning can be accomplished by cloning a polynucleotide insert molecule comprising a 5'-OH group at one end of the molecule and a 5'-phosphate group at the other end into a nucleic acid vector. For example, an insert polynucleotide (I) with a 5'OH group at one end and a 5'-phosphate at the other end can be cloned into a linear cloning vector, where the linear cloning vector has a topoisomerase polypeptide covalently joined at one end and a ligation substrate site at the other end. The insert polynucleotide, the linear cloning vector, and a ligase are incubated together under conditions sufficient for their covalent joining to form a ligated circular vector (a ligated insert/vector molecule). The circular vector can then be transformed into a host cell.

Directional cloning can also be accomplished by cloning an insert polynucleotide having a 5'-OH group on one end and a 5'-phosphate group on the other end into a vector where the vector comprises, for example, two vector arm molecules comprising a topoisomerase polynucleotide at only one end and a cloning substrate site at the other end. For example, a first vector arm, LVA, is covalently joined to an insert molecule at the 5'-OH end by incubating a LVA and an insert molecule together under conditions sufficient to permit topoisomerase-mediated covalent joining to form a ligated nucleic acid molecule where the insert molecule is positioned adjacent to a LVA to create LVA-I-phosphate. The 5'-phosphate end of the insert is unable to be ligated to the LVA or RVA because a topoisomerase polypeptide is joined to the LVA and RVA at the 5'-phosphate. The LVA-I-5'-phosphate is treated with phosphatase, under conditions which permit removal of a 5'-phosphate group from the ligated nucleic acid resulting in a LVA-I-5'-OH molecule. The LVA-I-5'-OH molecule is then covalently joined to the RVA to form LVA-I-RVA by incubating a LVA-I-5'-OH molecule with a RVA under conditions which permit topoisomerase covalent joining to form a ligated molecule where the insert molecule is positioned between a RVA and a LVA (a ligated insert/vector molecule). Preferably, the cloning substrate site is a cos site, a LIC site, a loxP site, a site for homologous recombination, a site for site-specific recombination, or a ligation substrate site.

Alternatively, directional cloning can be accomplished with an insert polynucleotide comprising a 5'-OH group on one end and a 5'-phosphate group on the other end and two vector molecules. One vector molecule comprises a topoisomerase polynucleotide on only one end and a cloning substrate site on the other end. The other vector molecule comprises a ligation substrate site on one end and a cloning substrate site on the other end. An insert, a first vector molecule comprising a topoisomerase polypeptide at one end and a cloning substrate site at the other end, such as a LVA, and a second vector molecule such as a RVA comprising a ligation substrate site at one end and a cloning substrate at the other end are covalently joined by topoisomerase-mediated joining and ligase-mediated joining under conditions sufficient to form a ligated nucleic acid where the insert molecule is positioned between the LVA and the RVA vector molecules (a ligated insert/vector molecule). Preferably, the cloning substrate site is a cos site, a LIC site, a loxP site, a site for homologous recombination, a site for site-specific recombination, or a ligation substrate site.

Where the ligated insert/vector molecule comprises cos sites at each end, the linear molecule can be transformed directly into a host cell. Where the ligated insert/vector molecule comprises LIC ends at each end, the LIC ends can be annealed to a circular plasmid vector with LIC compatible ends. The circular molecule can be transformed into a host cell. Where the ligated insert/vector molecule comprises loxP sites on both ends, the ligated insert/vector molecule can be recombined into a circular plasmid in vitro in the presence of Cre recombinase. The recombinant circular plasmid can then be transformed into a host cell. Alternatively, a ligated insert/vector molecule with loxP sites at both ends of the molecule can be directly transformed into a host cell, such as *E. coli* harboring a plasmid suitable for site-specific recombination. The host cell may be rec A+ or recA−, and is preferably recA−. Where the covalently joined insert/vector molecule comprises sites for homologous recombination at each end, the covalently joined insert/vector molecule can be directly transformed into a suitable host cell harboring a plasmid suitable for homologous recombination.

The covalently joined insert/vector can be transformed into a prokaryotic or eukaryotic cell. Preferably, the covalently joined insert/vector is transformed into a prokaryotic host cell, such as a bacteria cell such as *E. coli*. Transformation of a ligated insert/vector molecule into a host cell can be done by any method known in the art. Methods for transformation of host cells can be found in Sambrook et al. and Ausubel and include, but are not limited to transfection, chemical transformation, electroporation, and lipofection. Where a bacteriophage lambda vector has been used according to the invention, the ligated insert/lambda vector can be packaged in vitro and then transfected into host cells, such as XL1-Blue *E. coli*. See e.g. Sambrook et al.

The following are provided for exemplification purposes only and are not intended to limit the scope of the invention described in broad terms above. All references cited in this disclosure are incorporated herein by reference.

EXAMPLES

Example 1

Inter-Molecular Ligation and Molecular Cloning Using Univalent Topoisomerase-Bound DNA An insert nucleic acid molecule, for example, a PCR product, can be generated by PCR using a primer set consisting of a 5'-primer and 3'-primer. Two vector nucleic acid molecules, for example, a left vector arm and a right vector arm are prepared such that a topoisomerase enzyme (TOPO) is covalently bound only to one end of a nucleic acid molecule to form a univalent topoisomerase vector molecule. PCR primers for generating an insert molecule can be synthesized to possess either a hydroxyl group or phosphate group at each of the 5'-ends. A hydroxyl group permits ligation to topoisomerase-bound DNA while a phosphate group prohibits such ligation.

For non-directional ligation of a PCR insert molecule to, for example two vector arms, both PCR primers will possess 5'-hydroxyl groups. The PCR insert can ligate with the vector arms to form four different types of ligation products: 1) left vector arm (LVA)-insert molecule (I)-left vector arm (LVA); 2) right vector arm (RVA)-insert (I)-right vector arm (RVA); 3) LVA-I-RVA; and 4) RVA-I-LVA. Only the LVA-I-RVA and RVA-I-LVA create viable replication competent entities (FIG. 1).

Figure 2:
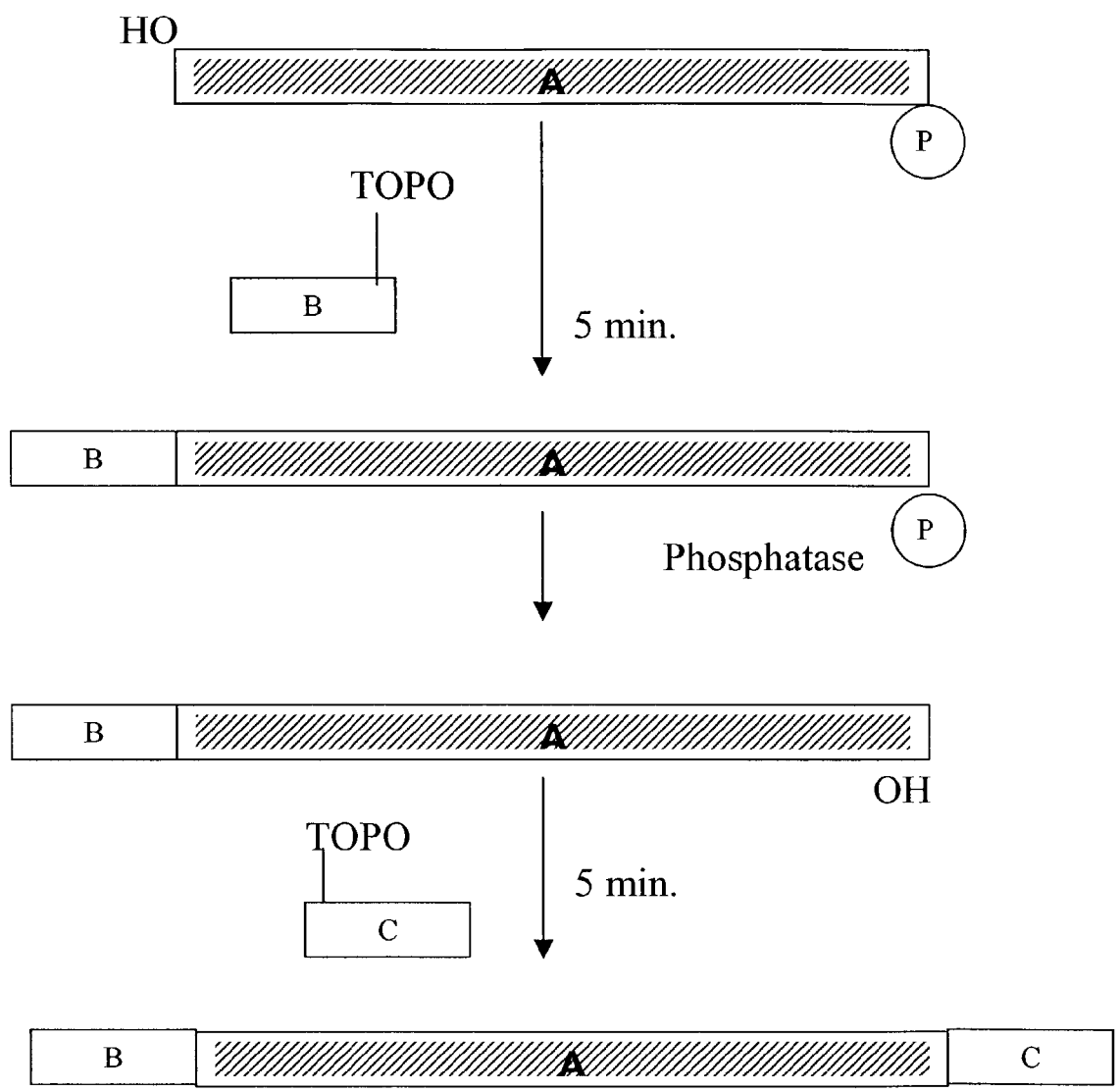
FIG. 2 shows the directional covalent joining of an insert molecule with a 5'-OH group on one end and a 5'-phosphate group on the other end to a right vector arm and a left vector arm each comprising a topoisomerase polypeptide on one end only.

For directional ligation of a PCR insert molecule to, for example, left and right vector arms, one PCR primer possesses a 5'-hydroxyl group and the other PCR primer possesses a 5'-phosphate group. The PCR generated insert molecule is generated and is first ligated to one vector arm, for example, a LVA to create a LVA-I-5'-phosphate molecule. The 5'-phosphate end of this molecule is unable to ligate to the LVA or RVA because the vector arm sites to which the TOPO is bound contain a 3'-phosphate. This molecule is then dephosphorylated to create to LVA-I-5'-OH. The LVA-I-5'-OH molecule is then ligated to the other vector arm (RVA) to form LVA-I-RVA (FIG. 2). Once the ligated insert/vector molecule described above has been constructed, the two vector arms can be non-covalently or covalently joined to one another, at the ends distal to the covalently attached topoisomerase polypeptide (i.e., their free ends), by a number of methods such that a circular molecule is formed. Such methods include, for example, ligase enzyme mediated ligation, complementary sequence annealing, topoisomerase mediated ligation, in vitro or in vivo site-specific recombination, or in vivo homologous recombination.

Example 2

Directional Molecular Cloning Using Topoisomerase and a Ligase Enzyme

Figure 3:
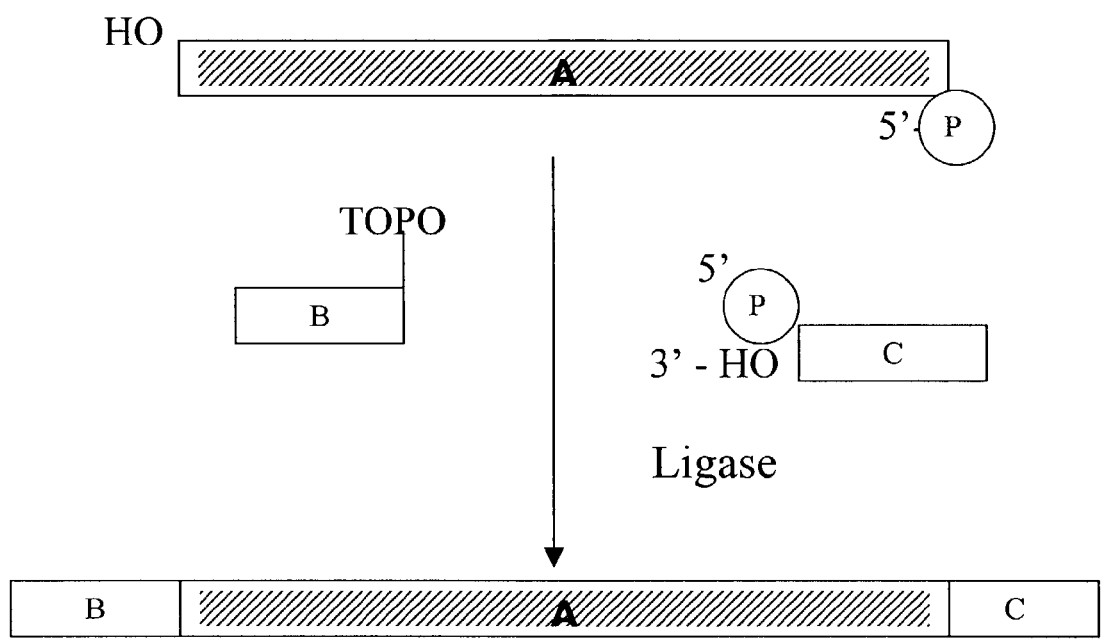
FIG. 3 shows the directional covalent joining of an insert molecule with a 5'-OH group on one end and a 5'-phosphate group on the other end to a left vector arm comprising a topoisomerase polypeptide on one end only and a right vector arm comprising a ligation substrate site on one end.

A nucleic acid insert is generated using, for example, a pair of PCR primers wherein one primer (P1) has a hydroxyl group at its 5'-end (OH-P1) and the other primer (P2) has a phosphate group at its 5'-end (P2-P) (see FIG. 3). The insert molecule is generated by PCR. A linear vector nucleic acid is prepared such that it has TOPO bound at one end (univalent TOPO-bound nucleic acid molecule); the other end of the linear vector nucleic acid comprises a substrate for ligation (a 3'-OH) to be mediated by a ligase enzyme. In a single incubation, the PCR insert can be ligated to the TOPO-end of the linear vector nucleic acid via TOPO-mediated ligation and to the other end of the linear vector nucleic acid via a ligase enzyme-mediated reaction. The product of the ligation is transformed into an appropriate host cell. A cloning event mediated by both topoisomerase and DNA ligase is unidirectional. The hydroxyl or phosphate group at the 5'-end of the PCR primers determines the directionality of the insert.

A second approach involving a topoisomerase- and ligase-mediated ligation comprises generation of an insert by for example, PCR. Where PCR is used to generate an insert, a pair of PCR primers where one has a hydroxyl group at its 5'-end (HO-P1) and the other has a phosphate group at its 5'-end (P2-P) (see FIG. 4). A vector, such as two vector nucleic acid arms, can be prepared such that one vector arm has a TOPO bound at one end (univalent TOPO-bound DNA molecule) and the other vector arm has a substrate for ligation at one end. In a single incubation, the PCR insert is ligated to the one vector arm with a TOPO end via TOPO-mediated ligation and to the other vector arm with the ligation-ready end via ligase enzyme-mediated reaction. The product of the ligation is transformed into an appropriate host cell. The cloning event mediated by both topoisomerase and DNA ligase is unidirectional. The hydroxyl or phosphate group at the 5'-end of the PCR primers determines the directionality. The other ends of the two vector arms are then joined by any of the methods described above. Using this cloning method the ligation products comprised of RVA-I-RVA or LVA-I-LVA should not be formed, but in the event that some do occur, such ligation products are incapable of subsequent replication and propagation.

Example 3

Molecular Cloning Using Topoisomerase and cos Ends

Figure 5:
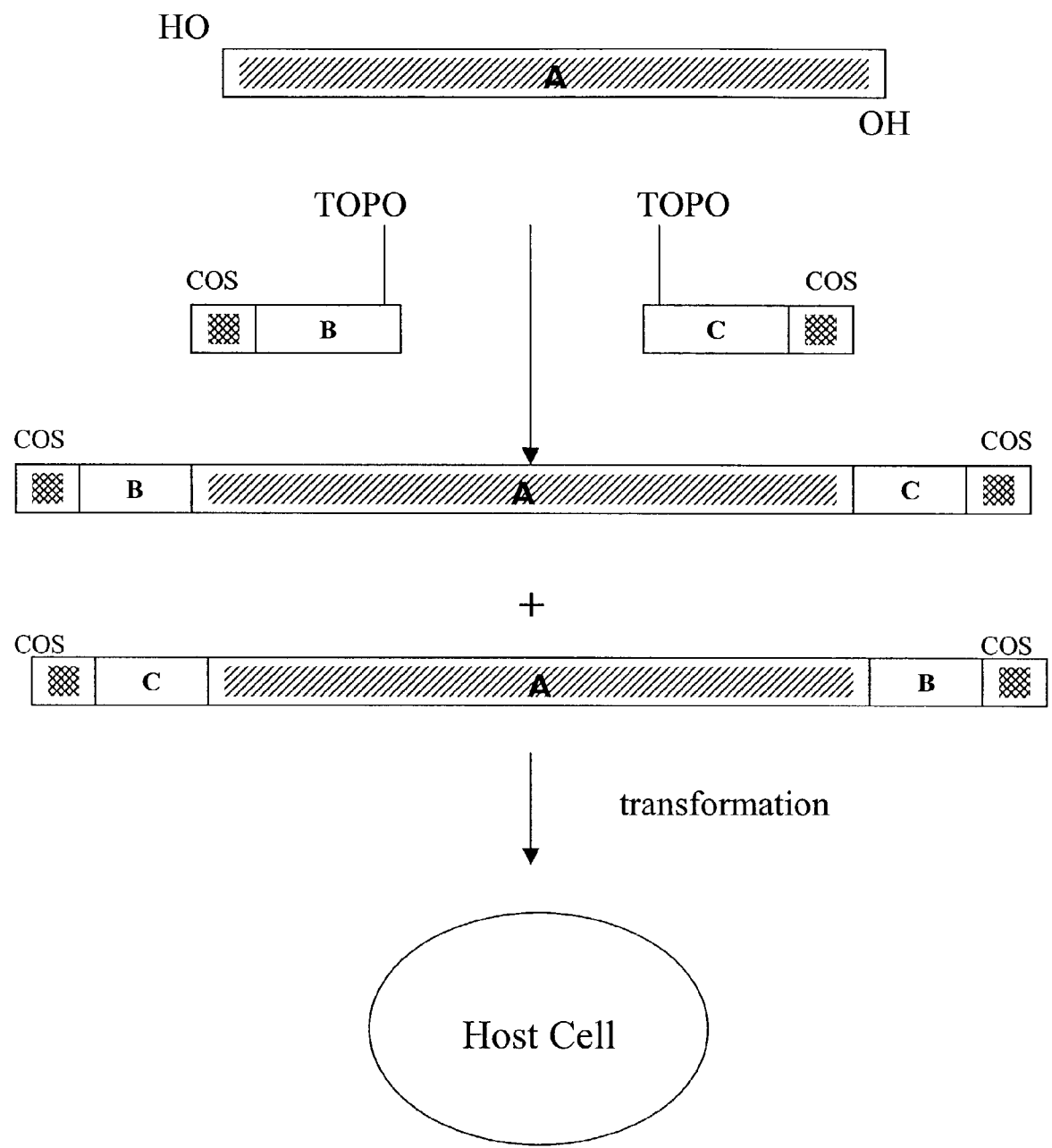
FIG. 5 shows the non-directional cloning of an insert molecule with 5'-OH groups on each end to a right vector arm and a left vector arm each comprising a topoisomerase polypeptide on one end only and a cloning substrate site, cos, on the other end.

A method of molecular cloning using topoisomerase and cos ends can comprise a vector, where such a vector may consist of two vector arms, with each arm consisting of one TOPO-end and one cos end. cos refers to the cohesive ends present at the termini of bacteriophage lambda. An insert, such as a PCR insert, can be generated using primers comprising 5'-OH termini. The PCR insert can be ligated to a TOPO-end of the two vector arms by DNA topoisomerase (see FIG. 5). Ligation events that result in LVA-I-LVA or RVA-I-RVA cannot subsequently be propagated. The product of the ligation can be transformed into a suitable host. The distal ends of the vector arms contain terminal cos sites that are readily annealed to one another in *E. coli* host cells by virtue of their explicit sequence. cos sites do not anneal in vitro at room temperature.

Figure 6:
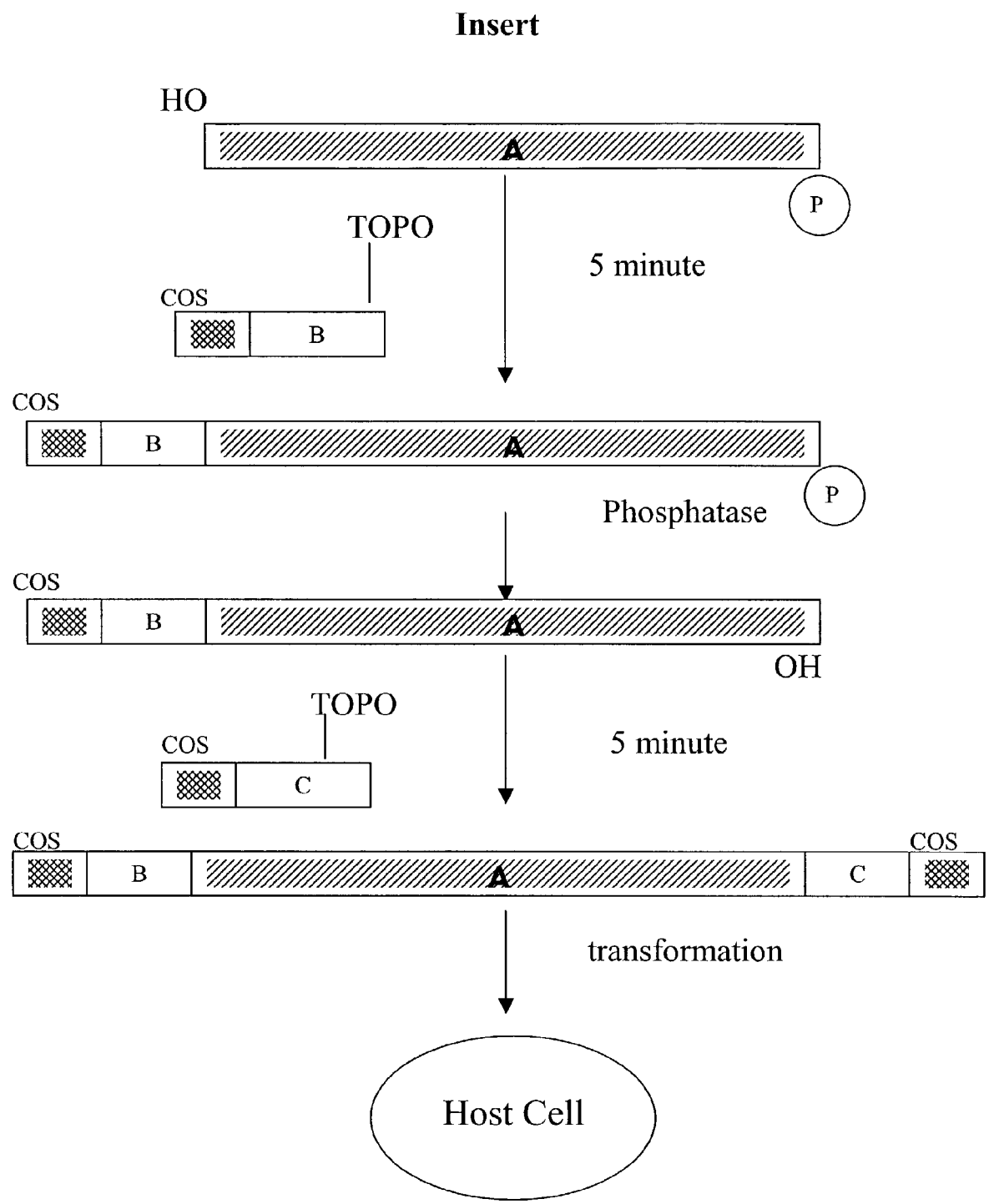
FIG. 6 shows the directional cloning of an insert molecule with a 5'-OH group on one end and a 5'-phosphate group on the other end to vector molecules comprising a topoisomerase polypeptide on one end only and a cloning substrate site, cos, on the other end.

This method of cloning can be directional or non-directional. In the case of non-directional cloning, an insert comprises a 5'-hydroxyl ends and can be ligated to, for example, two vector arms in a single reaction. For directional cloning, an insert can be generated by, for example, PCR wherein one PCR primer has a 5'-hydroxyl group and the other PCR primer has a 5'-phosphate group. Thus, the resulting PCR insert will contain one 5'-hydroxyl end and one 5'-phosphate end. The insert is to be ligated sequentially, first to a left vector arm containing a TOPO bound end followed by dephosphorylation of the 5'-phosphate of the insert and then ligation to the right vector arm containing a TOPO bound end (FIG. 6).

The ligation product of the insert to the vector is a linear molecule in vitro with two cos sequences at its end. It is transformed into a host, such as *E. coli* more efficiently than a circular molecule.

Example 4

Molecular Cloning Using Topoisomerase and LIC Ends

Figure 7:
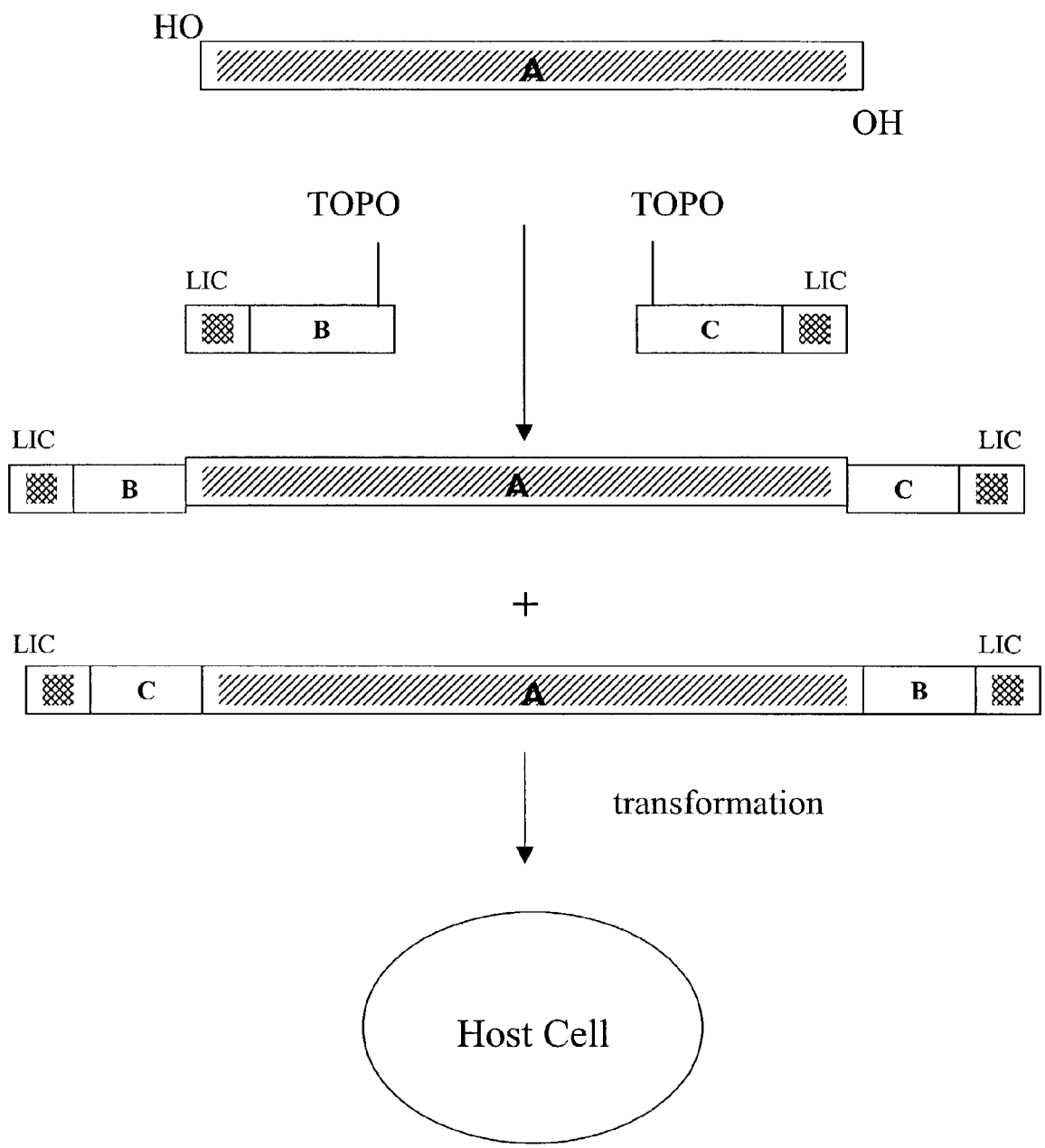
FIG. 7 shows the non-directional cloning of an insert molecule with 5'-OH groups on each end to a right vector arm and a left vector arm each comprising a topoisomerase polypeptide on one end only and a cloning substrate site, LIC, on the other end.

A method of molecular cloning using topoisomerase and LIC ends can comprise a vector, such as two vector arms, each consisting of one TOPO-end and one LIC end. An insert, such as a PCR insert, can be generated using primers comprising two 5'-OH termini. The PCR insert can be ligated to a TOPO-end of the two vector arms by DNA topoisomerase (see FIG. 7). Ligation events that result in LVA-I-LVA or RVA-I-RVA cannot subsequently be propagated. The distal ends of the vector arms contain terminal LIC sites that are readily annealed to a plasmid comprising LIC compatible ends.

Figure 8:
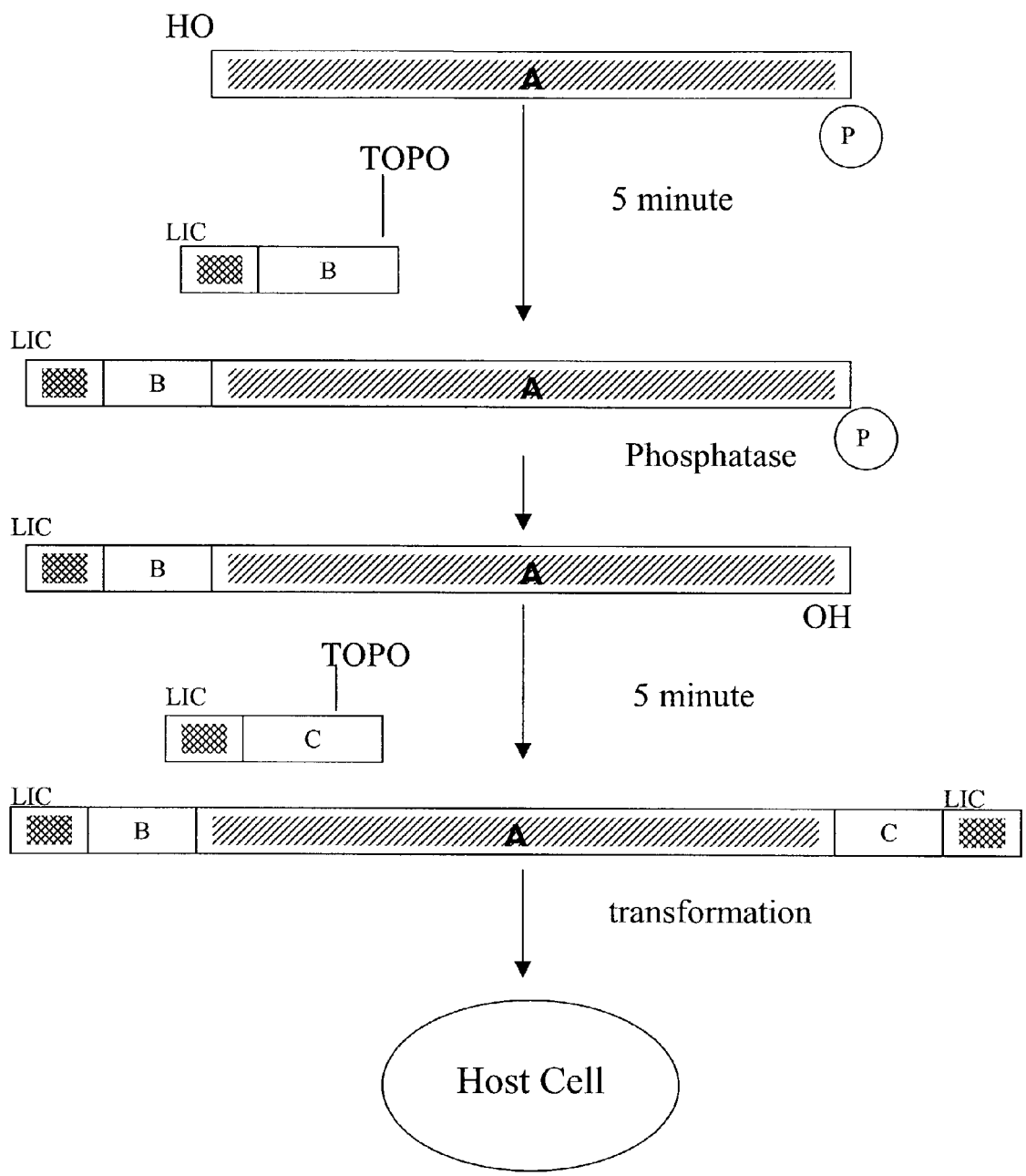
FIG. 8 shows the directional cloning of an insert molecule with a 5'-OH group on one end and a 5'-phosphate group on the other end to vector molecules comprising a topoisomerase polypeptide on one end only and a cloning substrate site, LIC, on the other end.

This method of cloning can be directional or non-directional. In the case of non-directional cloning, an insert comprising 5'-hydroxyl ends and can be ligated to, for example, two vector anus in a single reaction. For directional cloning, an insert can be generated by, for example, PCR wherein one PCR primer has a 5'-hydroxyl group and the other PCR primer has a 5'-phosphate group. Thus, the resulting PCR insert will contain one 5'-hydroxyl end and one 5'-phosphate end. The insert is to be ligated sequentially, first to the left vector arm containing a TOPO bound end and followed by dephosphorylation of the 5'-phosphate of the insert and then ligation to the right vector arm containing a TOPO bound end (FIG. 8).

Example 5

Molecular Cloning into Lambda Vector

Figure 9:
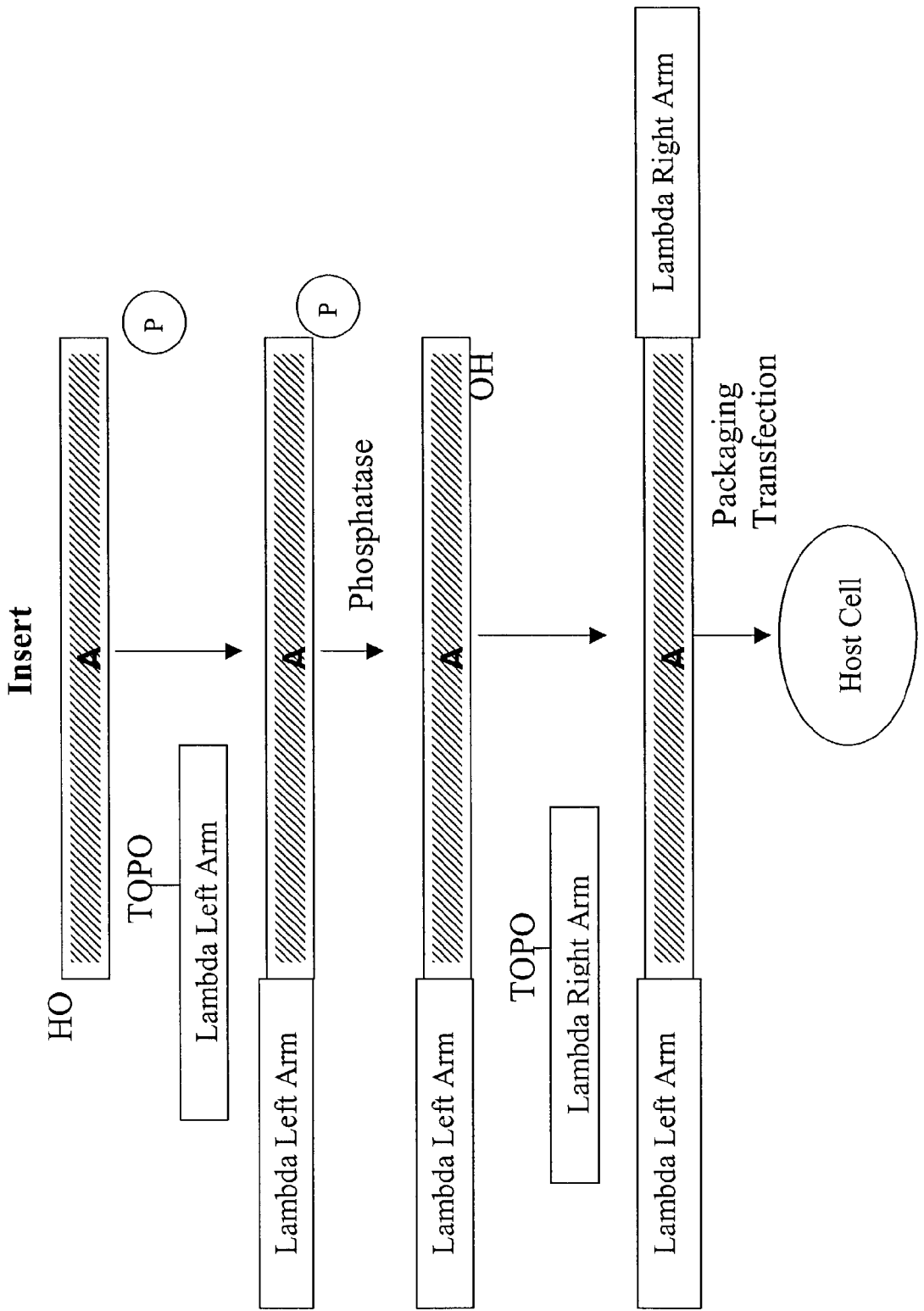
FIG. 9 shows the directional cloning of an insert molecule with a 5'-OH group on one end and a 5'-phosphate group on the other end to vector molecules comprising a topoisomerase polypeptide on one end only of a lambda vector arm.

The vector can comprise lambda DNA vector arms (termed left lambda arm (LLA)) and right lambda arm (RLA)). An insert, such as a PCR generated insert, can be ligated to the lambda vector arms in a directional manner or non-directional manner. In the case of non-directional cloning, a PCR insert can be generated using 5'-hydroxyl PCR primers. The insert can be ligated to two lambda vector arms in a single reaction. Ligation events resulting in LLA-I-LLA or RLA-I-RLA cannot subsequently be propagated. For directional cloning, one PCR primer has a 5'-hydroxyl end and the other PCR primer has a 5'-phosphate end. Thus, the PCR insert is comprised of one 5'-hydroxyl end and one 5'-phosphate end. The insert can be ligated sequentially to the two lambda vector arms with a dephosphorylation step in between as depicted in FIG. 9. The ligated lambda construct can be packaged in vitro and transfected into host cells such as XLI-Blue *E. coli*. A circular plasmid DNA containing the insert of interest can be rescued from the lambda vector using, for example, ZAP technology (Stratagene).

Example 6

Molecular Cloning Into a Linear Plasmid DNA Molecule

Figure 10:
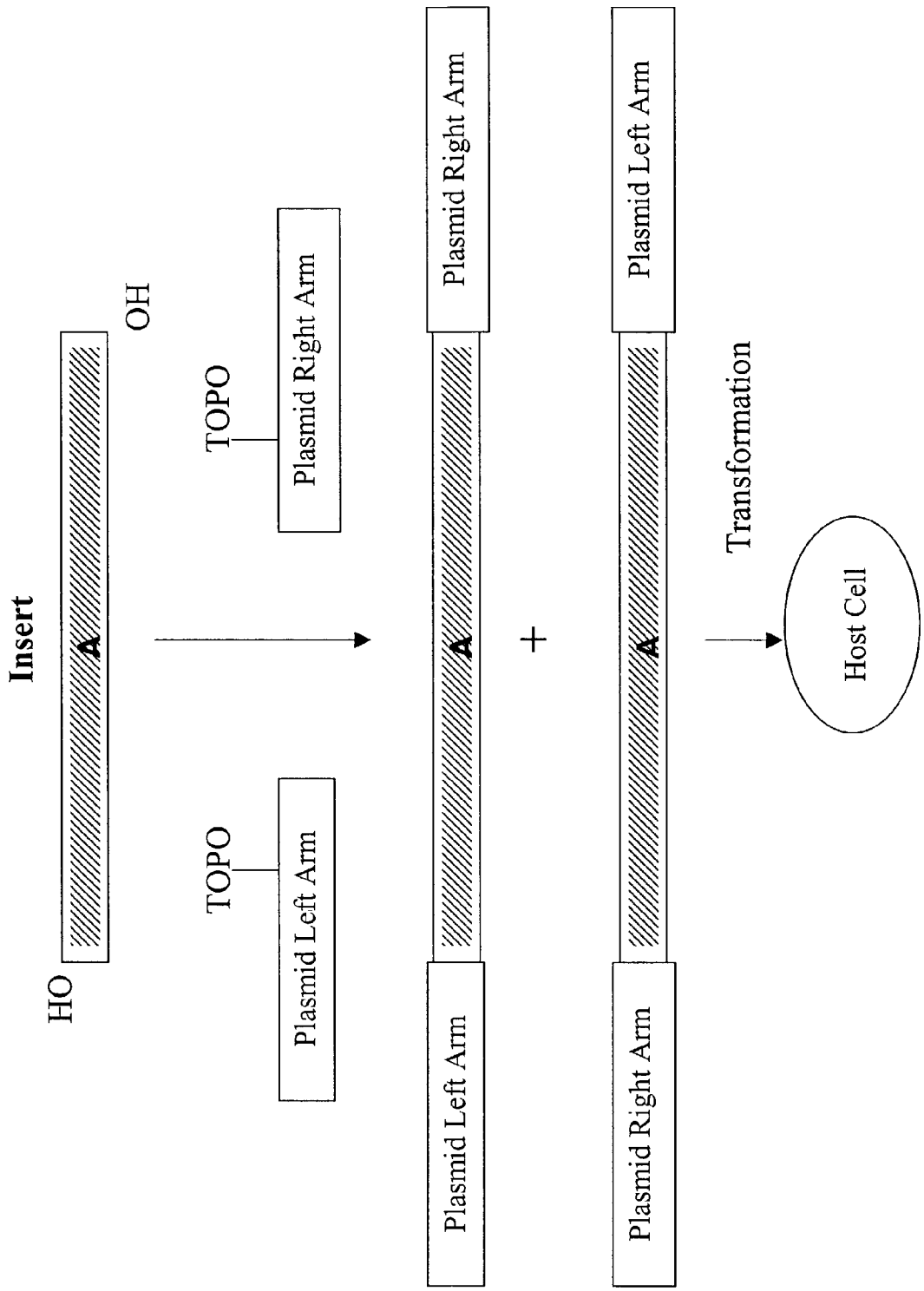
FIG. 10 shows the non-directional cloning of an insert molecule with 5'-OH groups on each end to a right plasmid arm and a left plasmid arm each comprising a topoisomerase polypeptide on one end only.
Figure 11:
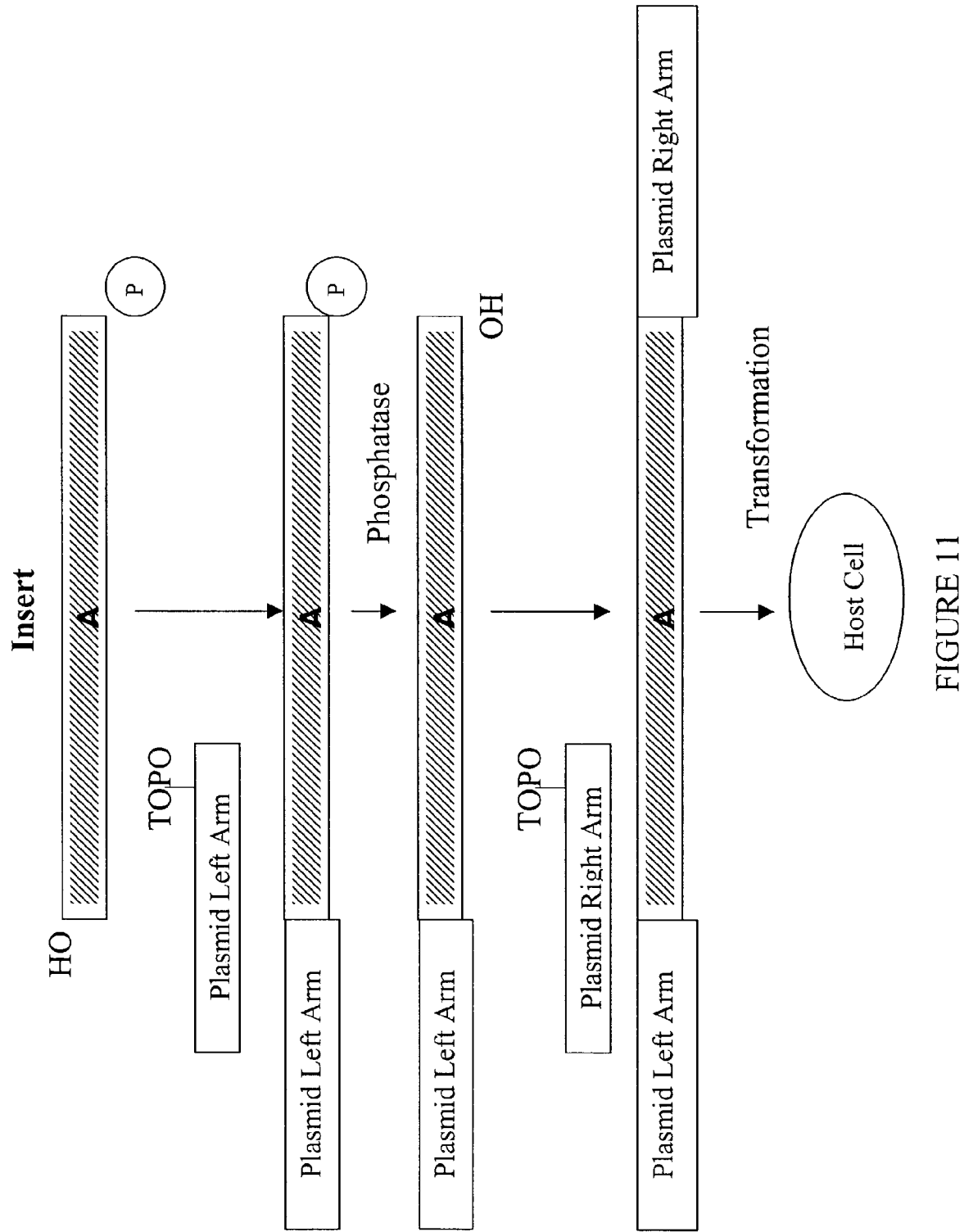
FIG. 11 shows the directional cloning of an insert molecule with a 5'-OH group on one end and a 5'-phosphate group on the other end to vector molecules comprising a topoisomerase polypeptide on one end only.

A vector can comprise vector arms of a linear plasmid such as N15. An insert, such as a PCR generated insert, can be ligated to the plasmid vector arms in a directional manner or non-directional manner. In the case of non-directional cloning, a PCR insert can be generated using 5'-hydroxyl PCR primers. The insert can be ligated to two plasmid vector arms in a single reaction (FIG. 10). Ligation events resulting in LVA-I-LVA or RVA-I-RVA cannot subsequently be propagated. For directional cloning, one PCR primer has a 5'-hydroxyl end and the other PCR primer has a 5'-phosphate end. Thus the PCR insert is comprised of one 5'-hydroxyl end and one 5'-phosphate end. The insert can be ligated sequentially to the two plasmid vector arms with a dephosphorylation step in between as depicted in the FIG. 11. The linear DNA can be transformed directly into *E. Coli*. Alternatively, the ligated plasmid construct can be packaged in vitro and transfected into host cells such as XLI-Blue *E. coli*. A DNA containing the insert of interest can be rescued from the vector using, for example, ZAP technology (Stratagene).

Figure 4:
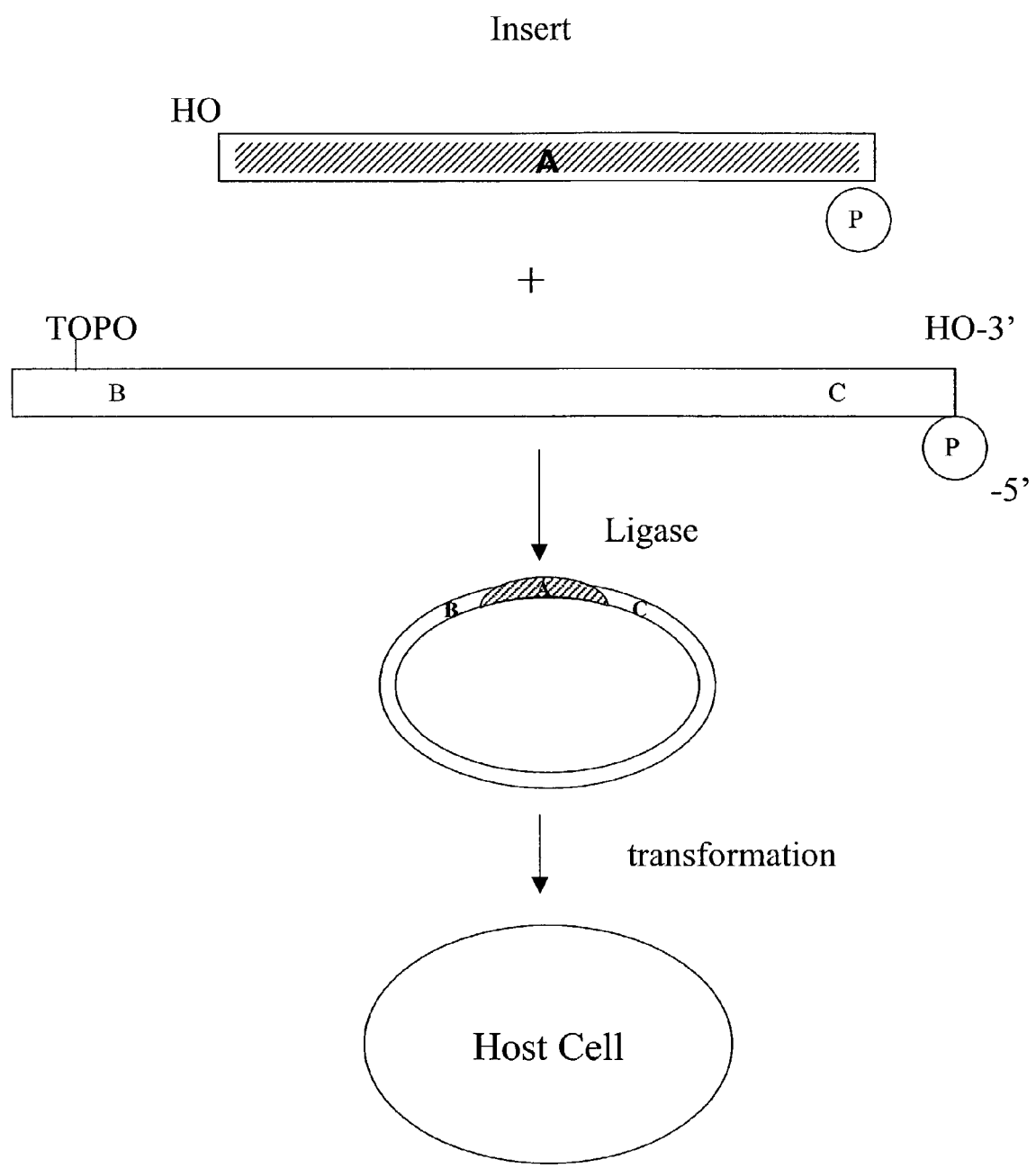
FIG. 4 shows the directional cloning of an insert molecule with a 5'-OH group on one end and a 5'-phosphate group on the other end to a linear vector molecule. The linear vector molecule comprises a topoisomerase molecule on one end only and a ligation substrate site on the other end.

A vector can also comprise a linear plasmid vector consisting of a covalently bound topoisomerase polypeptide at one end and a ligation substrate site at the other end (see FIG. 4). Incubation of the vector with an insert molecule comprising 5'-OH group on one end and a 5'-phosphate group on the other end, under conditions sufficient for topoisomerase-mediated ligation and ligase enzyme-mediated ligation results in a ligated circular plasmid comprising the insert molecule. The plasmid can be transformed into a host cell.

Example 7

Molecular Cloning Using Topoisomerase and Site-Specific Recombination

Figure 12:
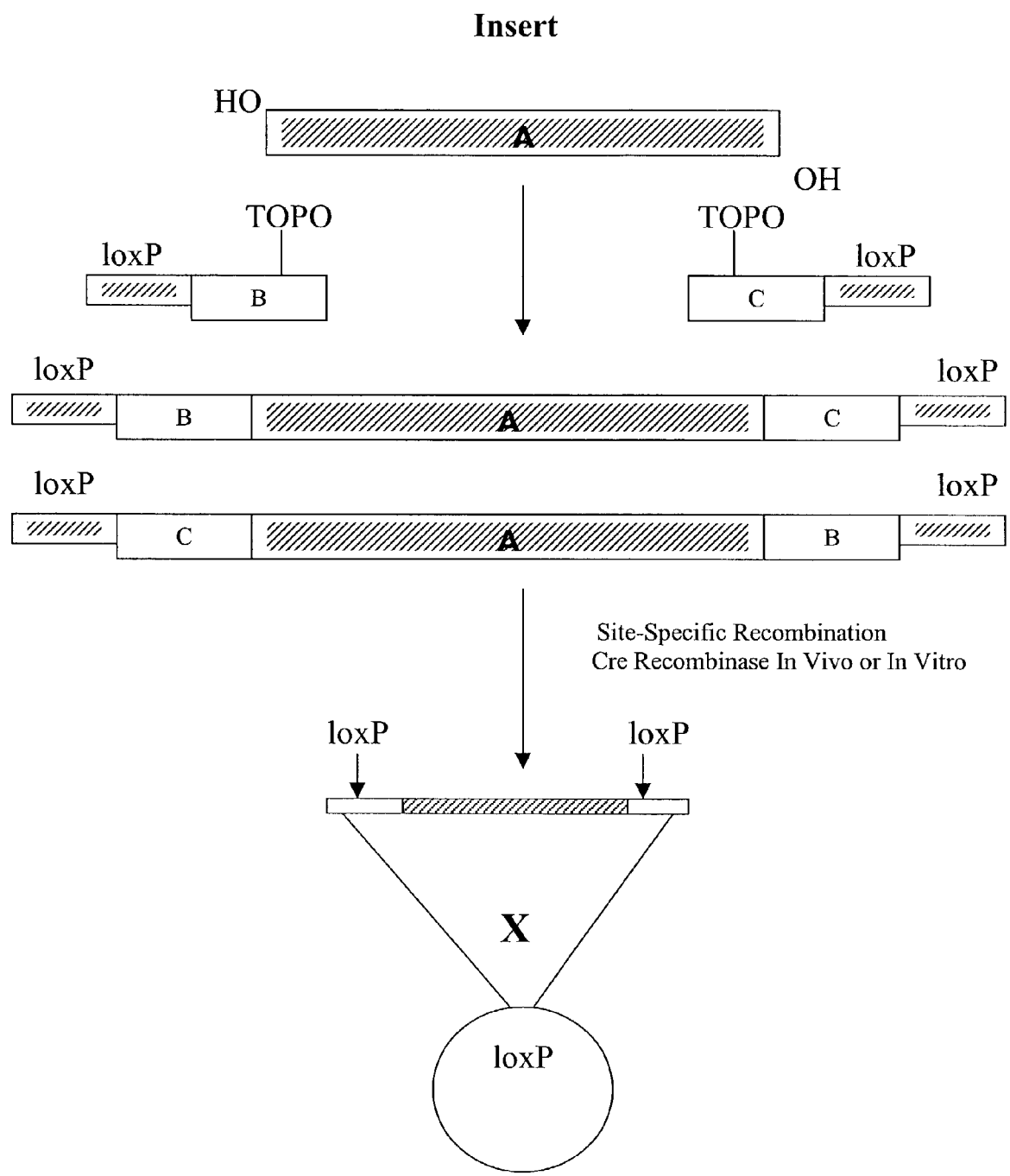
FIG. 12 shows the non-directional cloning of an insert molecule with 5'-OH groups on each end to a right vector arm and a left vector arm each comprising a topoisomerase polypeptide on one end only and a cloning substrate site, a loxP site, on the other end.
Figure 13:
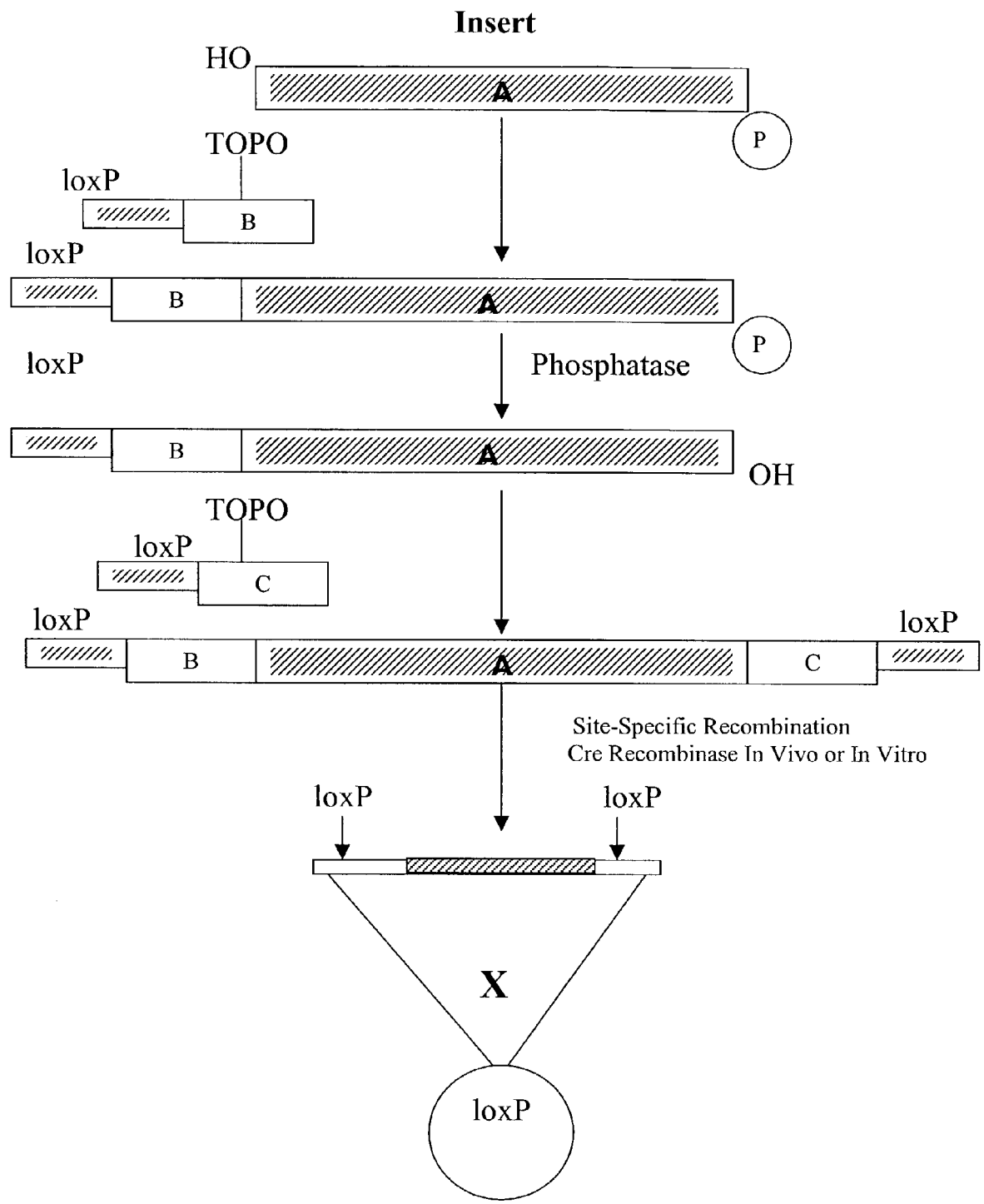
FIG. 13 shows the directional cloning of an insert molecule with a 5'-OH group on one end and a 5'-phosphate group on the other end to vector molecules comprising a topoisomerase polypeptide on one end only and a cloning substrate site, a loxP site, on the other end.

A vector can comprise vector arms that comprise one TOPO-end and one loxP end. The loxP site can be recombined with a second loxP site in the presence of a Cre site-specific recombination protein. An insert, such as a PCR generated insert, can be ligated to the TOPO-end of the two vector arms. Such cloning can be directional or non-directional. In the case of non-directional cloning, an insert, such as a PCR insert can be generated from PCR primers each comprising 5'-hydroxyl ends. An insert comprising two 5'-OH ends can be ligated to two vector arms in a single reaction (FIG. 12). For directional cloning, an insert can be generated by, for example, PCR wherein one PCR primer comprises a 5'-hydroxyl end and the other PCR primer comprises 5'-phosphate end resulting in an insert that comprises one 5'-hydroxyl end and one 5'-phosphate end. The insert can be ligated sequentially to two vector arms with a dephosphorylation step in between as depicted in FIG. 13. The ligation product comprises a loxP site at each end of a linear molecule. The linear molecule can be recombined into a circular recombinant plasmid in vitro, for example using purified Cre recombinase or in vivo by, for example transformation into an E. coli host expressing Cre recombinase and a plasmid that has loxP sites.

Example 8

Molecular Cloning Using Topoisomerase and Homologous Recombination in Vivo

Figure 14:
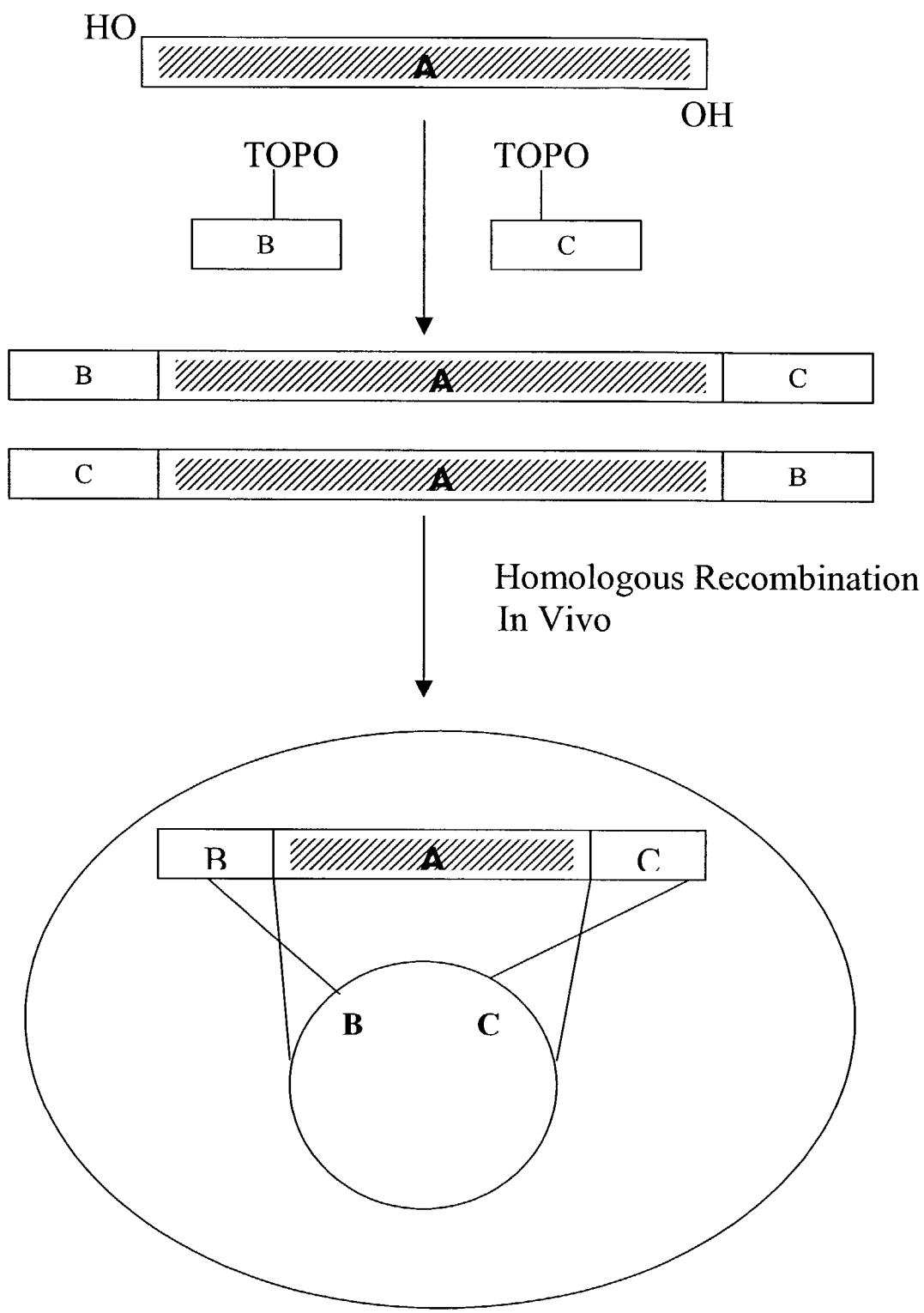
FIG. 14 shows the non-directional cloning of an insert molecule with 5'-OH groups on each end to a right vector arm and a left vector arm each comprising a topoisomerase polypeptide on one end only and a cloning substrate site, a site for homologous recombination, on the other end.
Figure 15:
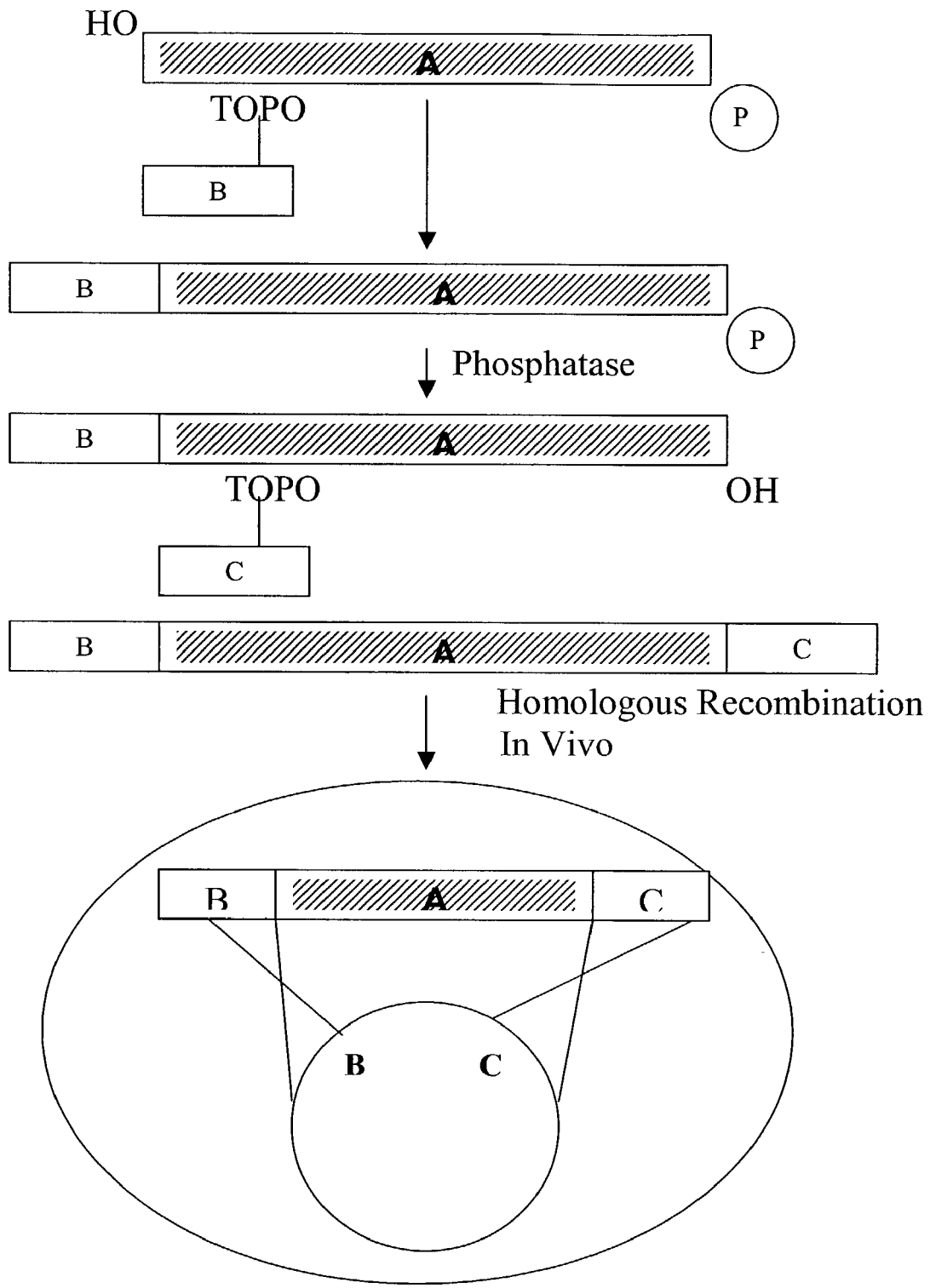
FIG. 15 shows the directional cloning of an insert molecule with a 5'-OH group on one end and a 5'-phosphate group on the other end to vector molecules comprising a topoisomerase polypeptide on one end only and a cloning substrate site, a site for homologous recombination, on the other end.

In vivo homologous recombination can be exploited to transfer a ligated insert/vector of interest into a circular plasmid vector. Homologous sequences flank a ligated insert/vector of interest and are substantially identical to sequences of a plasmid cloning vector. A ligated insert/vector of interest is recombined into a plasmid cloning vector of choice via homologous recombination between the homologous sequences flanking the ligated insert/vector and in the plasmid cloning vector. An insert can be generated with homologous sequences attached to each end by, for example, synthesizing PCR primers with homologous vector sequences, of for example, 30, 75, 100, 150, 200, 250, 500, or 1000 base pairs and using the PCR primers to generate a ligated insert/vector with homologous vector sequences flanking the ligated insert/vector of interest. A ligated insert/vector molecule with homologous sequences at the ends can also be generated by preparing topoisomerase-bound homologous sequence elements and employing a TOPO cloning scheme as outlined in FIGS. 14 and 15 for generating an insert with homologous sequence elements on each end. A PCR amplified insert containing TOPO ligated arms can be transformed into host cells containing a cloning vector wherein homologous recombination can occur. For efficient in vivo homologous recombination, a recA+ host strain can be used. To protect a linear insert from degradation by endogenous exonuclease activities, the ends of the insert can be modified to either inhibit or prohibit exonuclease digestion events.

To achieve site-specific in vivo recombination, lambda attachment sites can be employed in place of the homologous sequences described above. In this scenario, lambda attachment sites flank a ligated insert/vector of interest, which is generated according to the PCR and TOPO cloning schemes described above. The ligated insert/vector with the flanking lambda attachment sites is transformed into host cells containing a cloning vector with lambda attachment sites. Inside the host cell, the ligated insert/vector then can be site-specifically recombined into a plasmid cloning vector between the lambda attachment sites flanking the ligated insert/vector and those sites in the plasmid cloning vector.

OTHER EMBODIMENTS

Other embodiments are within the following claims.

We claim:

1. A method of molecular cloning, wherein a nucleic acid insert molecule is covalently joined to first and second double stranded nucleic acid flanking molecules to form a ligated molecule, the method comprising:
   (A) incubating said insert molecule and said flanking molecules, wherein each end of said insert molecule comprises a 5'-hydroxyl group, and wherein one end only of each of said first and second flanking molecules comprises a covalently bound topoisomerase polypeptide, under conditions which permit their covalent joining to form a ligated molecule comprising a said insert molecule positioned between a said first and a said second flanking molecule; and
   (B) transforming the covalently joined insert molecule of step (a) into a host cell to obtain transformants.

2. The method of claim 1, wherein a said first and a said second nucleic acid flanking molecules comprise a left and a right vector arm, respectively, such that a said insert molecule is flanked by a said left vector arm and a said right vector arm.

3. The method of claim 2, wherein said left and right vector arms each comprise a free end that is not joined to an insert molecule, said method further comprising the step of:
   joining the free ends of said vector arms to each other by a method selected from the group consisting of nucleic acid ligase mediated ligation, complementary sequence annealing, topoisomerase mediated ligation, in vitro site-specific recombination, in vivo site-specific recombination, and in vivo homologous recombination.

4. A method of molecular cloning comprising:
   (A) incubating a nucleic acid insert molecule comprising a 5'-hydxoxyl group at one end and a 5'-phosphate at the other end, and a linear double stranded cloning vector, wherein the linear cloning vector comprises a covalently bound topoisomerase polypeptide at one end only and a ligation substrate site at the other end, under conditions sufficient for the covalent joining of said insert to said vector to form a ligated circular vector comprising said linear cloning vector and said insert molecule; and
   (B) transforming the ligated circular vector of step (A) into a host cell to obtain transformants.

5. The method of claim 3 wherein said joining of the free ends of said left and right vector arms comprises in vivo site-specific recombination.

6. The method of claim 5 wherein the free end of each of said left and right vector arms that is not joined to said insert molecule comprises a loxP site, and wherein said transforming step (B) comprises transforming the covalently joined molecule of step (A) into a host cell comprising Cre recombinase, wherein said transforming results in in vivo site-specific recombination between the free end of said left vector arm and the free end of said right vector arm to generate a circularized vector molecule.

* * * * *